US012708786B2

(12) United States Patent
Siedenburg et al.

(10) Patent No.: US 12,708,786 B2
(45) Date of Patent: Aug. 18, 2026

(54) MONITORING ARTERIAL AND VENOUS BLOOD FLOW DURING TREATMENTS

(71) Applicant: Stryker Corporation, Kalamazoo, MI (US)

(72) Inventors: Clinton T. Siedenburg, Everett, WA (US); Fred W. Chapman, Newcastle, WA (US); Daniel W Piraino, Seattle, WA (US); Tyson G. Taylor, Bothell, WA (US)

(73) Assignee: Stryker Corporation, Portage, MI (US)

(*) Notice: Subject to any disclaimer, the term of this patent is extended or adjusted under 35 U.S.C. 154(b) by 0 days.

(21) Appl. No.: 18/431,374

(22) Filed: Feb. 2, 2024

(65) Prior Publication Data

US 2024/0260926 A1 Aug. 8, 2024

Related U.S. Application Data

(60) Provisional application No. 63/443,301, filed on Feb. 3, 2023.

(51) Int. Cl.

| | |
|---|---|
| ***A61N 1/39*** | (2006.01) |
| ***A61B 8/00*** | (2006.01) |
| ***A61B 8/06*** | (2006.01) |
| ***A61H 31/00*** | (2006.01) |
| ***A61N 1/02*** | (2006.01) |

(52) U.S. Cl.

CPC ............ *A61N 1/39044* (2017.08); *A61B 8/06* (2013.01); *A61B 8/4236* (2013.01); *A61B 8/461* (2013.01); *A61B 8/488* (2013.01); *A61B 8/5223* (2013.01); *A61H 31/004* (2013.01); *A61N 1/02* (2013.01);

(Continued)

(58) Field of Classification Search

CPC .... A61N 1/39044; A61N 1/02; A61N 1/3925; A61B 8/06; A61B 8/4236; A61B 8/461; A61B 8/488; A61B 8/5223; A61B 5/026; A61B 5/0261; A61B 5/14553; A61B 5/4064; A61B 8/0808; A61B 8/42; A61B 8/4227; A61B 8/481; A61H 31/004;

(Continued)

(56) References Cited

U.S. PATENT DOCUMENTS

| | | | |
|---|---|---|---|
| 3,658,060 | A | 4/1972 | Eklof |
| 10,729,615 | B2 | 8/2020 | Taylor et al. |

(Continued)

FOREIGN PATENT DOCUMENTS

| | | | |
|---|---|---|---|
| WO | WO2015073903 | A1 | 5/2015 |
| WO | WO2017056042 | A1 | 4/2017 |

(Continued)

OTHER PUBLICATIONS

Search Report for European Patent Application No. 24155547.3, dated May 24, 2024, 7 pages.

(Continued)

*Primary Examiner* — Bo Joseph Peng
(74) *Attorney, Agent, or Firm* — Lee & Hayes, P.C.

(57) ABSTRACT

An example method includes detecting blood flow in an artery of a subject and detecting blood flow in a vein of the subject. The example method further includes determining whether blood is spontaneously flowing through the body of the subject by comparing the blood flow through the artery and the blood flow through the vein.

20 Claims, 9 Drawing Sheets

(52) U.S. Cl.
CPC ...... *A61N 1/3925* (2013.01); *A61H 2230/255* (2013.01)

(58) Field of Classification Search
CPC ...... A61H 2230/255; A61H 2201/5097; A61H 2230/305; A61H 31/005
See application file for complete search history.

(56) References Cited

U.S. PATENT DOCUMENTS

| | | | |
|---|---|---|---|
| 10,918,354 B2 | 2/2021 | Nichol et al. | |
| 11,272,901 B2 | 3/2022 | Torp et al. | |
| 11,324,476 B2 | 5/2022 | Eibl et al. | |
| 11,717,255 B2 | 8/2023 | Torp et al. | |
| 12,226,253 B2 | 2/2025 | Torp et al. | |
| 2008/0273709 A1 | 11/2008 | Thiagarajan et al. | |
| 2010/0022886 A1 | 1/2010 | Ayati et al. | |
| 2010/0298899 A1 | 11/2010 | Donnelly et al. | |
| 2011/0245651 A1 | 10/2011 | Nakamura | |
| 2012/0226163 A1 | 9/2012 | Moehring et al. | |
| 2013/0006111 A1* | 1/2013 | Sasaki | A61B 8/5246 600/440 |
| 2015/0190109 A1 | 7/2015 | Christensen et al. | |
| 2015/0297107 A1 | 10/2015 | Sullivan et al. | |
| 2017/0196465 A1 | 7/2017 | Browning et al. | |
| 2017/0224581 A1 | 8/2017 | Johnson et al. | |
| 2018/0153514 A1 | 6/2018 | Zhai et al. | |
| 2018/0199834 A1 | 7/2018 | Siedenburg | |
| 2018/0353157 A1 | 12/2018 | Eibl et al. | |
| 2019/0053975 A1 | 2/2019 | von Schenck et al. | |
| 2019/0209085 A1 | 7/2019 | Freeman et al. | |
| 2020/0113455 A1 | 4/2020 | Kato | |
| 2021/0045967 A1* | 2/2021 | Lampe | A61H 31/007 |
| 2021/0059638 A1 | 3/2021 | Rodriquez | |
| 2021/0169736 A1 | 6/2021 | Wijshoff et al. | |
| 2022/0000447 A1 | 1/2022 | Eibl et al. | |
| 2022/0054008 A1 | 2/2022 | Venkatraman et al. | |
| 2022/0142858 A1 | 5/2022 | Wijshoff et al. | |
| 2022/0280378 A1 | 9/2022 | Kaufman et al. | |
| 2023/0011862 A1 | 1/2023 | Eibl et al. | |
| 2023/0048327 A1 | 2/2023 | Lampe et al. | |
| 2024/0000427 A1 | 1/2024 | Eibl et al. | |
| 2024/0260895 A1 | 8/2024 | Siedenburg et al. | |
| 2024/0261179 A1 | 8/2024 | Siedenburg et al. | |
| 2024/0261583 A1 | 8/2024 | Siedenburg et al. | |
| 2024/0261584 A1 | 8/2024 | Siedenburg et al. | |

FOREIGN PATENT DOCUMENTS

| | | |
|---|---|---|
| WO | WO2017072626 A1 | 5/2017 |
| WO | WO2017211814 A1 | 12/2017 |
| WO | WO2022157761 A1 | 7/2022 |
| WO | WO2024200766 A1 | 10/2024 |

OTHER PUBLICATIONS

Search Report for European Patent Application No. 24155568.9, dated May 31, 2024, 8 pages.
Search Report for European Patent Application No. 24155498.9, dated Jun. 4, 2024, 6 pages.
Search Report for European Patent Application No. 24155581.2, dated Jun. 5, 2024, 9 pages.
Search Report for European Patent Application No. 24155536.6, dated Jul. 4, 2024, 9 pages.
Nagahara, et al., "In Vivo Measurement of Blood Velocity in Human Major Retinal Vessels Using the Laser Speckle Method," Retina, Investigative Ophthalmology & Visual Science, Jan. 2011, vol. 52, No. 1, pp. 87-92.
Rader, et al., "An Interferometric Blood Flow Measurement Technique—A Brief Analysis," IEEE Transactions on Biomedical Engineering, vol. BME-21, Issue: 4, Jul. 1974, pp. 293-297.
Rajan, et al., "Review of methodological developments in laser Doppler flowmetry," Lasers Med Sci, 24:269-283, Mar. 2009.

* cited by examiner

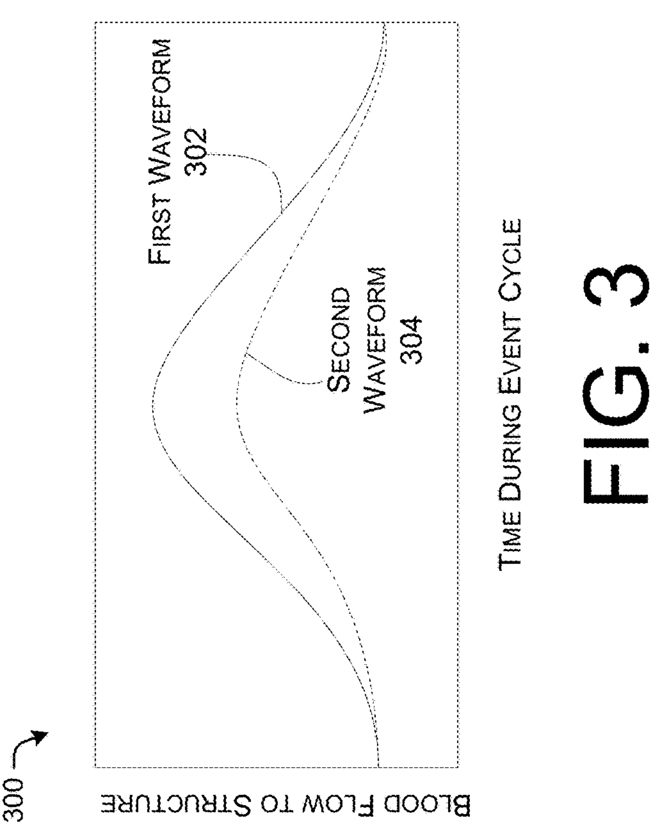
FIG. 3
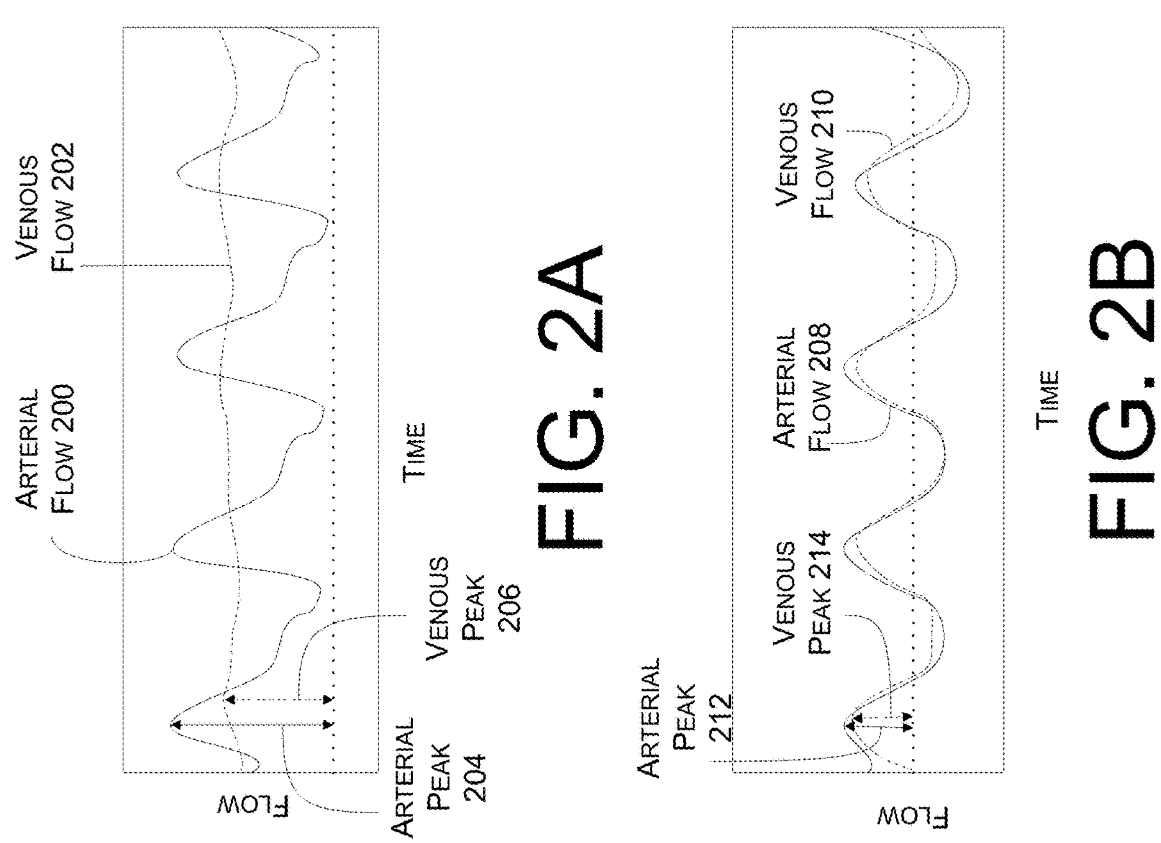
FIG. 2A
FIG. 2B

MONITORING ARTERIAL AND VENOUS BLOOD FLOW DURING TREATMENTS

CROSS-REFERENCE TO RELATED APPLICATION

This application claims priority to U.S. Provisional App. No. 63/443,301, which is titled "Blood Flow Monitors," was filed on Feb. 3, 2023, and is hereby incorporated by reference in its entirety.

BACKGROUND

When a subject experiences cardiac arrest, their heart is unable to effectively pump blood through their circulatory system. Without blood circulation, the subject may experience hypoxic injuries, such as brain damage, or even death. A rescuer can temporarily achieve blood circulation in the subject by administering chest compressions manually or via a mechanical chest compression device. If applied effectively, chest compressions can push blood through the subject's circulatory system until the subject regains spontaneous blood circulation. Thus, chest compressions can at least temporarily prevent hypoxic injuries due to cardiac arrest.

BRIEF DESCRIPTION OF THE DRAWINGS

FIGS. 2A and 2B illustrate waveforms of blood flow through veins and arteries with respect to time. FIG. 2A illustrates waveforms of blood spontaneously flowing through an example artery and an example vein with respect to time. FIG. 2B illustrates waveforms of blood flowing through an example artery an example vein with respect to time due to the application of chest compressions.

FIG. 3 illustrates an example graphical user interface (GUI) element that portrays a changing condition of a subject over multiple cycles of an event.

DETAILED DESCRIPTION

Figure 1:
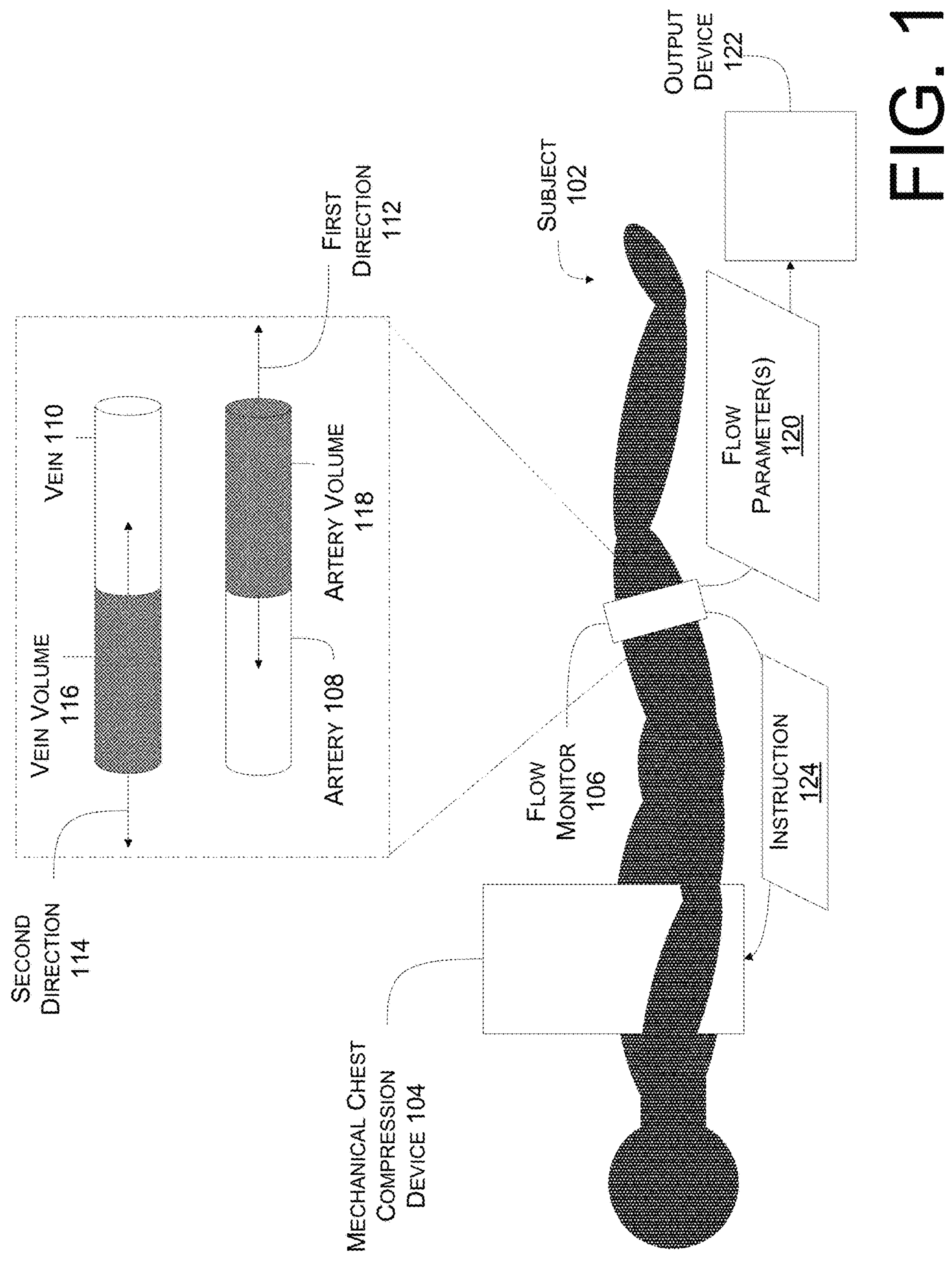
FIG. 1 illustrates an example environment for assessing the condition of a subject by monitoring arterial and venous blood flow.

Various implementations described herein relate to techniques for assessing a treatment administered to a subject (e.g., a human subject, patient, or other animal) by non-invasively monitoring arterial and venous blood flow. Various implementations described herein also relate to techniques for assessing a condition of the subject based on the arterial and venous blood flow.

In particular cases, a flow monitor detects blood flow through in artery and/or a vein of the subject. The artery and vein may be paired, such that they carry oxygenated blood toward and deoxygenated blood from a common physiological structure when the subject has spontaneous circulation (e.g., when the heart of the subject is effectively pumping blood through the subject's body, also referred to as "heart-induced circulation"). In various cases, the flow monitor detects the blood flow by detecting a Doppler shift, or other discrepancy, between an incident beam (e.g., ultrasound or light) directed toward the blood and a reflection of the incident beam from the blood. The incident beam, for instance, propagates through the skin of the subject, such that the flow monitor can noninvasively detect blood flow in the subject while being disposed outside of the subject's body.

Various functionality is enabled by monitoring the arterial and venous blood flow. In some cases, the efficacy of a treatment (e.g., chest compressions) can be assessed based on the arterial and venous blood flow. In some examples, spontaneous circulation of blood through the body of the subject can be detected, or even distinguished from flow due to chest compressions, using various techniques described herein. Accordingly, the flow monitor can provide real-time feedback of the subject's condition. Such feedback enables the rescuer (or a mechanical chest compression device administering chest compressions) to efficiently and effectively adjust chest compression parameters in order to optimize an amount of blood flow induced by the chest compressions. In some cases, the flow monitor notifies the rescuer (or mechanical chest compression device) when blood begins to spontaneously circulate in the subject's body, such that the rescuer (or mechanical chest compression device) can quickly pause chest compressions as the subject's heart begins to effectively pump blood.

Implementations of the present disclosure are directed to improvements in the technical field of subject monitoring, particularly in emergency medical settings. Some technologies can monitor chest compression effectiveness indirectly, using non-blood flow parameters like blood oxygenation that can be used to estimate whether chest compressions are pushing blood through the circulatory system of a subject. In some cases, inadequate chest compressions would be indicated by non-blood flow parameters after a significant delay because they are indirect estimates of chest compression effectiveness. As a result, a subject receiving inadequate (e.g., misplaced) chest compressions could suffer severe hypoxic injury without a rescuer efficiently identifying the source of the problem in a timely fashion. According to various implementations of the present disclosure, the effectiveness of ongoing chest compressions can be directly assessed by detecting and analyzing arterial and/or venous blood flow.

Other improvements are described herein. Because both chest compressions and a pumping heart generate blood flow, it was difficult for some previous technologies to be able to tell whether a subject receiving chest compressions experienced ROSC by monitoring blood flow. In contrast, various implementations of the present disclosure enable accurate detection of spontaneous circulation during chest compression administration, such as by simultaneously monitoring arterial and venous blood flow.

As used herein, the terms "blood flow," "blood flow parameters," and their equivalents, may refer to one or more physiological parameters indicative of a movement of blood through a blood vessel. For example, the term "blood velocity" may refer a change in position with respect to time (i.e., distance per time, such as meters per second) of one or more blood cells moving in a blood vessel. The term "blood speed" may refer to a magnitude of a velocity (i.e., distance per time) of one or more blood cells moving in a blood vessel. The term "velocity profile," for example, may refer to a velocity of blood in a blood vessel with respect to a location within the blood vessel, such as a velocity of blood in a blood vessel with respect to a location along a cross-section of the blood vessel. The term "flow rate," and its equivalents, may refer to a volume or mass of blood that passes a boundary (e.g., a cross-section of a blood vessel) with respect to time. The terms "net flow," "net flow volume," and their equivalents, may refer to a volume or mass of blood that passes a boundary during a discrete time interval, such as during a cardiac cycle. A net flow volume can be calculated by integrating a flow rate over the time interval. Unless otherwise specified explicitly or by context, the term "blood flow" may refer to blood velocity, blood speed, velocity profile, flow rate, net flow, or any other flow-related parameter described herein.

Implementations of the present disclosure will now be described with reference to the accompanying figures.

FIG. 1 illustrates an example environment 100 for assessing the condition of a subject 102 by monitoring arterial and venous blood flow. In some instances, the example environment 100 is a non-clinical setting. For example, the example environment 100 may be a location outside of a hospital, such as an indoor public space (e.g., airport terminal, school, office building, train station, or the like). In some cases, however, the example environment 100 is within a clinical setting, such as a hospital or medical clinic.

In various examples, the subject 102 is experiencing a medical emergency, such as cardiac arrest. For instance, the heart of the subject 102 is not effectively pumping blood throughout the body of the subject 102. As a result, the subject 102 may lack a pulse. As used herein, the term "pulse," and its equivalents, refers to pulsatile and spontaneous blood circulation through one or more blood vessels due to blood pumping from a heart. In some cases, the subject 102 is experiencing an arrhythmia (e.g., ventricular fibrillation (VF), pulseless ventricular tachycardia (VT), or the like) that prevents the heart from spontaneously pumping blood through the body of the subject 102.

Various devices may be utilized to treat and/or monitor the subject 102 during the medical emergency. In various cases, a mechanical chest compression device 104 is configured to administer chest compressions to the subject 102. In various implementations, a rescuer (not illustrated) physically positions the mechanical chest compression device 104 around the body of the subject 102. In some cases, the rescuer operates the mechanical chest compression device 104 directly and causes the mechanical chest compression device 104 to administer the chest compressions using a compressor. In some cases, the compressor includes a plunger that moves up-and-down on the chest of the subject 102. In some examples, the compressor includes a band that tightens and loosens around the chest of the subject 102. Based on the operation of the mechanical chest compression device 104, a periodic pressure is administered to the chest of the subject 102, which can cause blood to flow periodically throughout the body of the subject 102 while the heart of the subject 102 is unable to effectively pump the blood.

When placed correctly, the mechanical chest compression device 104 can effectively induce blood flow through the body of the subject 102 in order to prevent hypoxic injury to the brain, other vital organs, and other tissues of the subject 102. However, if the mechanical chest compression device 104 is administering the chest compressions to an ineffective position on the chest of the subject 102, the chest compressions may be unable to effectively move blood through the body of the subject 102. For example, the mechanical chest compression device 104 may be ineffective if it administers compressions to a shoulder of the subject 102, or at some position that is relatively distant from the heart of the subject 102. Thus, there is a chance that the subject 102 may suffer a hypoxic injury from ineffective chest compressions during the medical emergency. It would therefore be beneficial to monitor circulation throughout the body of the subject 102 while the mechanical chest compression device 104 is administering chest compressions, in order to determine whether the chest compressions are effective.

Furthermore, there are other potential problems with the application of the mechanical chest compression device 104. In some cases, the subject 102 experiences a return of spontaneous circulation (ROSC) after the mechanical chest compression device 104 begins to administer chest compressions. For instance, after the heart of the subject 102 is administered an electrical shock by a defibrillator (not illustrated), the heart of the subject 102 may transition from VF to a heart rhythm that enables the subject 102 to regain a pulse. When the heart of the subject 102 regains the ability to sufficiently pump blood through the body of the subject 102, the chest compressions administered by the mechanical chest compression device 104 may no longer be needed to prevent hypoxic injury. At this point, additional chest compressions could cause unnecessary harm to the subject 102. For instance, the chest compressions could mechanically break bones or blood vessels in the subject 102, or otherwise damage the body of the subject 102. In some examples, the chest compressions could induce an arrhythmia in the subject 102. For example, a chest compression that deforms the heart during a particular interval in the cardiac cycle can induce VF. Thus, it is preferred to cease administering chest compressions immediately when the subject 102 experiences ROSC.

In various implementations of the present disclosure, a flow monitor 106 addresses these and other problems. The flow monitor 106 is configured to monitor an effectiveness of the chest compressions administered by the mechanical chest compression device 104 by detecting blood flow through an artery 108 of the subject 102 and/or blood flow through a vein 110 of the subject 102. Furthermore, in some implementations, the flow monitor 106 is configured to detect ROSC based on the blood flow through the artery 108 and/or the blood flow through the vein 110. In some cases, the flow monitor 106 initiates an analysis of whether the subject 102 has spontaneous circulation in response to receiving, from an external device (e.g., a defibrillator), a communication signal indicating that another treatment (e.g., defibrillation) has been administered to the subject 102.

In some examples, when the heart of the subject 102 effectively pumps blood, the artery 108 supplies blood to a physiological structure of the subject 102 and the vein 110 carries blood from the physiological structure of the subject 102. The physiological structure, for instance, is an organ, limb, appendage, or another type of body part. Examples of the physiological structure include a liver, a kidney, a pancreas, a stomach, a brain, a bladder, a gall bladder, an intestine (e.g., small intestine or large intestine), an esophagus, a stomach, an adrenal gland, a reproductive organ, a finger, a hand, an arm, a forearm, a toe, a foot, a calf, a leg, a head, a neck, a shoulder, a hip, or any combination thereof. Examples of the artery 108 include an aorta, a carotid artery, a pulmonary artery, a brachiocephalic artery, a thyroid artery, a laryngeal artery, a pericardial artery, a bronchial artery, a vertebral artery, an occipital artery, a cervical artery, a thoracic artery, a lingual artery, a thyroid artery, a facial artery, a temporal artery, a cerebral artery, a diploic artery, an emissary artery, an azygos artery, a subclavian artery, an axillary artery, a cephalic artery, a basilic artery, a brachial artery, an ulnar artery, a radial artery, a phrenic artery, a lumbar artery, a hepatic artery, a renal artery, an ovarian artery, a testicular artery, an iliac artery, a saphenous artery, a femoral artery, a cystic artery, a gastric artery, or a splenic artery. Examples of the vein 110 include a pulmonary vein, a vena cava, a brachiocephalic vein, a thyroid vein, a laryngeal vein, a pericardial vein, a bronchial vein, a vertebral vein, an occipital vein, a cervical vein, a thoracic vein, a jugular vein, a lingual vein, a thyroid vein, a laryngeal vein, a facial vein, a retromandibular vein, a cerebral vein, a diploic vein, an emissary vein, an azygos vein, a subclavian vein, an axillary vein, a cephalic vein, a basilic vein, a brachial vein, an ulnar vein, a radial vein, a phrenic vein, a lumbar vein, a hepatic vein, a renal vein, an ovarian vein, a testicular vein, an iliac vein, a saphenous vein, a femoral vein, a cystic vein, a gastric vein, a hepatic portal vein, or a splenic vein. In various examples, the artery 108 and the vein 110 are substantially parallel to one another within the body of the subject 102.

In some cases, the rescuer positions the flow monitor 106 on skin of the subject 102. The position of the flow monitor 106 on the subject may enable the flow monitor 106 to detect blood flow through the artery 108 and the vein 110. In some examples, the flow monitor 106 is adhered to the skin of the subject 102. In some cases, the flow monitor 106 is strapped to, or tied around, a limb of the subject 102.

In various examples, the flow monitor 106 is configured to detect blood flow using a Doppler-based technique. For instance, the flow monitor 106 may emit an incident beam (e.g., ultrasound, light, or the like) toward the blood in the artery 108 and the blood in the vein 110. The blood, in various cases, reflects or otherwise scatters the incident beam. A portion of the incident beam that is reflected from the blood in the artery 108 may be detected by the flow monitor 106. Further, a portion of the incident beam that is reflected from the blood in the vein 110 may be detected by the flow monitor 106. In various cases, the flow monitor 106 is configured to determine whether the blood is moving, and how fast the blood is moving, based on the reflections of the incident beam. For instance, the flow monitor 106 is configured to compare the phase and/or frequency of the reflections with the phase and/or frequency of the incident beam. Based on the comparison, the flow monitor 106 may determine the presence of movement, or specifically quantify the movement, of the blood in the artery 108 and/or vein 110. Various techniques for detecting blood flow are described below with reference to FIG. 4.

In some cases, the flow monitor 106 specifically distinguishes that the artery 108 is an artery and the vein 110 is a vein. For example, after being applied to the body of the subject 102, the flow monitor 106 may be configured to detect two blood vessels including the artery 108 and the vein 110. The flow monitor 106 may be able to determine that one blood vessel is the artery 108 and one blood vessel is the vein 110 using various techniques. In some cases, the flow monitor 106 distinguishes between the artery 108 and the vein 110 based on relative thicknesses of the walls of the artery 108 and the vein 110. For instance, the flow monitor 106 may determine that the blood vessel with the thicker walls is the artery 108 and the blood vessel with the thinner walls is the vein 110. In some examples, the flow monitor 106 distinguishes between the artery 108 and the vein 110 based on a relative collapsibility of the artery 108 and the vein 110. For instance, the flow monitor 106 may apply pressure to the skin of the subject 102, which is transferred to the blood vessels under the surface of the skin. In various cases, the flow monitor 106 may determine that the blood vessel that retains a relatively cylindrical shape despite the pressure is the artery 108 and that the blood vessel that has a compressed cross-section from the pressure is the vein 110. In various implementations, the flow monitor 106 includes an ultrasound transducer configured to generate B-mode images of the blood vessels, and performs segmentation (e.g., edge detection segmentation) on the B-mode images in order to identify the walls of the blood vessels and/or the cross-sectional shapes of the blood vessels. In some implementations, the identify of the artery 108 as an artery and the vein 110 as a vein are unnecessary to perform various analyses. Optionally, the flow monitor 106 does not specifically recognize the artery 108 as an artery and the vein 110 as a vein in these implementations, and merely detects blood flow in one or more blood vessels including the artery 108 and/or the vein 110.

According to some examples, the flow monitor 106 is configured to detect a direction of the blood flowing through the artery 108 and a direction of the blood flowing through the vein 110. For instance, the flow monitor 106 may determine whether the blood in the artery 108 and/or vein 110 is flowing in a first direction 112 or a second direction 114. The first direction 112 is a direction along the circulatory system of the subject 102 that points away from the heart of the subject 102. The second direction 114 is a direction along the circulatory system of the subject 102 that points toward the heart of the subject 102.

In various cases, the direction of the blood flow through the artery 108 and/or vein 110 indicates whether chest compressions are effectively pushing blood through the body of the subject 102. If the subject 102 lacks spontaneous circulation and is receiving ineffective chest compressions, or if the subject 102 is not receiving chest compressions, then the blood in the artery 108 and/or vein 110 may lack directionality. For example, the blood may be static and/or may follow a turbulent flow pattern indicating that blood is not being perfused through the body of the subject 102. In some examples, the flow monitor 106 determines that the mechanical chest compression device 104 is administering ineffective chest compressions by determining that the blood in the artery 108 and/or vein 110 is not moving in the first direction 112 or the second direction 114.

When the artery 108 and the vein 110 are located outside of the chest, the administration of effective chest compressions may induce (simultaneous) parallel flow through the artery 108 and the vein 110. For example, when the chest of the subject 102 is compressed, the compression pushes blood through the artery 108 and the vein 110 in the first direction 112 away from the heart of the subject 102. When the compression is released (e.g., during recoil), the blood spontaneously flows through the artery 108 and the vein 110 in the second direction 114 toward the heart of the subject 102. Thus, the flow monitor 106 may determine that effective chest compressions are being administered to the subject 102 by determining that blood in both the artery 108 and the vein 110 is moving in the first direction 112 or the second direction 114.

In some examples, the flow monitor 106 is configured to determine that the subject 102 has ROSC based on the directionality of the blood in the artery 108 and the vein 110. When the heart of the subject 102 is spontaneously pumping blood through the body of the subject 102, the blood in the artery 108 primarily moves in the first direction 112 and the blood in the vein 110 primarily moves in the second direction 114. That is, (simultaneous) antiparallel blood flow through the artery 108 and vein 110 is indicative of spontaneous blood circulation. In various implementations, the flow monitor 106 is configured to detect ROSC by determining that blood in the artery 108 is flowing in a different direction than blood in the vein 110.

In various cases, the flow monitor 106 is configured to detect a velocity of blood flowing through a cross-section of the artery 108 and a velocity of blood flowing through a cross-section of the vein 110. The cross-sections, for instance, may be substantially circular and be defined along circumferences of the artery 108 and vein 110. According to some cases, the cross-sections are ovoid and non-perpendicular to the first direction 112 and the second direction 114. In examples in which blood is flowing laminarly through the artery 108 and vein 110, the velocity profile of the blood along each cross-section may be at a maximum in the center of the cross-section and at a minimum along the edge of the cross-section.

The blood velocities through the artery 108 and vein 110, at any position along the cross-sections of the artery 108 and vein 110, may be indicative of the effectiveness of the chest compressions. The flow monitor 106, for instance, may determine that the chest compressions are ineffective by determining that at least one velocity through the artery 108 and/or the vein 110 is below at least one threshold. In some cases, the flow monitor 106 determines that the chest compressions are effective by determining that at least one velocity through the artery 108 and/or the vein 110 is above at least one threshold. In some examples, the flow monitor 106 determines a peak velocity and/or a mean velocity of blood through the artery 108 and/or the vein 110 during a time period. For instance, the flow monitor 106 compares the peak velocity or the mean velocity of the artery 108 to a first threshold and/or the peak velocity or the mean velocity of the vein 110 to a second threshold. If any of these velocities is determined to exceed one or more thresholds, the flow monitor 106 may infer that the chest compressions are effectively pumping blood through the body of the subject 102. However, if any of these velocities is determined to be less than one or more thresholds, the flow monitor 106 may infer that the chest compressions are ineffective. In some cases, the time period during which the blood velocity is sampled is a time at which one or more chest compressions are administered to the subject 102.

In various cases, the flow monitor 106 is configured to detect a flow rate of blood flowing through the cross-section of the artery 108 and a flow rate of blood flowing through a cross-section of the vein 110. In examples in which blood is flowing laminarly through the artery 108 and vein 110, the velocity profile of the blood along each cross-section may be at a maximum in the center of the cross-section and at a minimum along the edge of the cross-section.

The flow rates through the cross-sections of the artery 108 and vein 110 may be indicative of the effectiveness of the chest compressions. The flow monitor 106, for instance, may determine that the chest compressions are ineffective by determining that at least one flow rate through the cross-section of the artery 108 and/or the cross-section in the vein 110 is below at least one threshold. In some cases, the flow monitor 106 determines that the chest compressions are effective by determining that at least one flow rate through the cross-section of the artery 108 and/or the cross-section in the vein 110 is above at least one threshold. In some examples, the flow monitor 106 compares a peak flow rate or a mean flow rate (over a time interval) along the cross-section of the artery 108 to a first threshold and/or a peak flow rate or a mean flow rate (over the time interval) along the cross-section of the vein 110 to a second threshold. In some cases, the time period during which the flow rate is sampled is a time at which one or more chest compressions are administered to the subject 102.

In various cases, the flow monitor 106 is configured to detect a net flow volume of blood that has flowed through the cross-section of the artery 108 and a net flow volume of blood flowed through a cross-section of the vein 110 during a time period. The net flow volumes through the cross-sections of the artery 108 and vein 110 may be indicative of the effectiveness of the chest compressions. The flow monitor 106, for instance, may determine that the chest compressions are ineffective by determining that at least one net flow volume through the cross-section of the artery 108 and/or the cross-section in the vein 110 is below at least one threshold. In some cases, the flow monitor 106 determines that the chest compressions are effective by determining that at least one net flow volume through the cross-section of the artery 108 and/or the cross-section in the vein 110 is above at least one threshold. In some cases, the time period during which the net flow volume is sampled is a time at which one or more chest compressions are administered to the subject 102.

According to some implementations, the flow monitor 106 is configured to optimize a chest compression parameter (e.g., rate, location, depth, recoil height, provider, etc.) by comparing measurements of a blood flow parameter (e.g., blood flow direction, blood velocity, volumetric flow rate, volume, etc.) before and after a modification of the chest compression parameter. For example, the flow monitor 106 may measure a peak blood velocity induced by chest compressions administered at a first location and a peak blood velocity induced by chest compressions administered at a second location. If the peak blood velocity at the first location is greater than the peak blood velocity at the second location, then the flow monitor 106 may indicate that the first location is a superior location for chest compressions compared to the second location.

In various implementations, the flow monitor 106 is configured to detect spontaneous circulation based on one or more blood velocities, flow rates, or net flow volumes through the artery 108 and/or vein 110. Outside of a medical emergency, the heart of the subject 102 is designed to pump blood in a pulsatile fashion in which the velocity and/or flow rate through a cross-section of the artery 108 with respect to time exhibits peaks that correspond to each heartbeat. In some cases, local maxima corresponding to both diastole and systole in velocity and/or flow rate are exhibited. When the heart is effectively pumping blood (e.g., the subject 102 lacks a significant arrhythmia, such as VF, supraventricular tachycardia (SVT), or pulsatile ventricular tachycardia (VT)), a time period between a local minimum and the proceeding peak of the velocity and/or flow rate with respect to time is shorter than a time period between the peak and the next local minimum. In various implementations, the heart of the subject 102 does not induce pulsatile flow in the vein 110 or at least does not induce as strong pulsatility in the vein 110 as the artery 108. In contrast, chest compressions may induce relatively equivalent pulsatile flow in both the artery 108 and the vein 110.

In various implementations, the flow monitor 106 is configured to detect spontaneous circulation in the subject 102 by evaluating the pulsatility of blood in the artery 108 and/or the vein 110. In various cases, pulsatility can be estimated based on a pulse amplitude of blood velocity or flow rate through a blood vessel. For example, the flow monitor 106 may identify an amplitude of a peak velocity or peak flow rate of blood through each of the artery 108 and vein 110 during a time period (e.g., during the administration of one or more chest compressions to the subject 102). The flow monitor 106, in some examples, determines a ratio of the amplitude of peak velocity or flow rate through the artery 108 with respect to the amplitude of peak velocity or flow rate through the vein 110. The flow monitor 106 may identify spontaneous circulation by determining that the ratio is greater than a threshold.

In some examples, the flow monitor 106 is configured to distinguish between spontaneous circulation and chest compression-induced circulation based on the pulsatility of blood flow through the vein 110. During spontaneous circulation without chest compressions, the blood flow through the vein 110 is non-pulsatile. However, during chest compressions, the blood flow through the vein 110 is pulsatile at a pulse frequency that is equivalent to the chest compression frequency. Therefore, in some cases, the flow monitor 106 may detect the administration of chest compressions to the subject 102 in response to determining that the pulsatility (e.g., amplitude of peak velocity or peak flow rate) through the vein 110 is above a threshold.

In some examples, the flow monitor 106 is configured to detect a vein volume 116, representing an amount of blood flowing through the cross-section of the vein 110 during a time interval. For example, the flow monitor 106 is configured to calculate and/or estimate the vein volume 118 by integrating the flow rate, velocity, or velocity profile through the cross-section of the vein 110 over a time interval. In some instances, the flow monitor 106 is configured to detect an artery volume 118 representing an amount of blood flowing through the cross-section of the artery 108 during the time interval. In various cases, the flow monitor 106 is configured to calculate and/or estimate the artery volume 118 by integrating the flow rate, velocity, or flow profile through the cross-section of the vein 110 over the time interval. The vein volume 116 is an example of a net flow of blood through the cross-section of the vein 110 during the time period. The artery volume 118 is an example of a net flow of blood through the cross-section of the artery 108 during the time period.

In general, circulation of blood caused by the heart of the subject 102 includes flow through the artery 108 in the first direction 112 and flow through the vein 110 in the second direction 114. This may be referred to as "anterograde flow." In contrast, circulation of blood caused by chest compressions administered to the subject 102 includes flow through the artery 108 and the vein 110 in the first direction 112 when the chest is compressed and in the second direction 114 when the chest is released. The flow of blood in the second direction 114 through the artery 108 and the flow of blood in the first direction 112 through the vein may be referred to as "retrograde flow." The vein volume 116, in various examples, represents an amount of blood that has passed through the cross-section of the vein 110 in which the second direction 114 is a positive direction and the first direction 112 is a negative direction. The artery volume 118, for instance, represents an amount of blood that has passed through the cross-section of the artery 108 in which the first direction 112 is a positive direction and the second direction 114 is a negative direction. Thus, the vein volume 116 and the artery volume 118, in various cases, may represent a net amount of anterograde flow through the vein 110 and artery 108, respectively.

The flow monitor 106 may detect an effectiveness of the chest compressions by comparing the artery volume 118 and/or the vein volume 116 to one or more thresholds. In various implementations, the flow monitor 106 calculates the artery volume 118 by integrating the velocity and/or flow rate through the cross-section of the artery 108 during a time interval that corresponds to the compression phase of a chest compression cycle. In various cases, the flow monitor 106 may determine that the chest compressions are effective by determining that the artery volume 118 defined during the compression phase is greater than a threshold. In contrast, the flow monitor 106 may determine that the chest compressions are ineffective by determining that the artery volume 118 defined during the compression phase is less than the threshold. In some cases, the flow monitor 106 determines the vein volume 116 by integrating the velocity and/or flow rate during a release phase of the chest compression cycle. For example, the flow monitor 106 may determine that the chest compressions are effective by determining that the vein volume 116 defined during the release phase is greater than a threshold and may determine that the chest compressions are ineffective by determining that the vein volume 116 is less than the threshold.

In various cases, the flow monitor 106 identifies the compression phase and/or the release phase of the chest compression cycle. In some cases, the mechanical chest compression device 104 may transmit a communication signal to the flow monitor 106 indicating the timing of the compression phase and/or the release phase. In some cases, the flow monitor 106 determines the compression phase as a time interval defined between a local minimum and a proceeding local maximum of the velocity and/or flow rate of blood through at least one of the blood vessels of the subject 102. In some examples, the flow monitor 106 determines the release phase as a time interval defined between a local maximum and a proceeding local minimum of the velocity and/or flow rate through at least one of the blood vessels of the subject 102.

The flow monitor 106 in some cases, may identify spontaneous circulation by determining an amount of anterograde flow through the artery 108 and/or vein 110. For instance, the flow monitor 106 may identify the presence of spontaneous circulation of blood through the body of the subject 102 by determining that the vein volume 116 is greater than a threshold and/or that the artery volume 118 is greater than a threshold. According to various examples, the flow monitor 106 may determine the vein volume 116 and the artery volume 118 by integrating the velocities and/or flow rates through the vein 110 and artery 108 over the same time period. This time period, for instance, may include a complete chest compression cycle (e.g., including a compression phase and a release phase of a chest compression). In some examples, the time period includes more than one chest compression cycle.

In some examples, the flow monitor 106 identifies spontaneous circulation in the body of the subject 102 by comparing an amount of anterograde and retrograde flow through the artery 108 and/or through the vein 110. In various examples, the vein volume 116 represents an amount of anterograde flow through the vein 110 and the artery volume 118 represents an amount of anterograde flow through the artery 108. The flow monitor 106 may further determine an amount of retrograde flow through the vein 110 and an amount of retrograde flow through the artery 108. For example, the amount of retrograde flow through the artery 108 may represent a volume of blood passing through the cross-section of the artery 108 in the second direction 114 (e.g., during a release phase of a chest compression cycle), and an amount of retrograde flow through the vein 110 may represent a volume of blood passing through the cross-section of the vein 110 in the first direction 112 (e.g., during a compression phase of a chest compression cycle). In various implementations, the flow monitor 106 determines a ratio of an amount of retrograde flow with respect to an amount of anterograde flow through the artery 108 and/or a ratio of an amount of retrograde flow with respect to an amount of anterograde flow through the vein 110. If the flow monitor 106 determines that either ratio is above a threshold (e.g., 0.1, 0.2, 0.3, or the like), then the flow monitor 106 may determine that blood is spontaneously circulating in the body of the subject 102.

In some implementations, the flow monitor 106 is configured to identify spontaneous flow by detecting a direction of the flow of blood in at least one blood vessel (e.g., the artery 108 or vein 110) over time. In some cases, the flow monitor 106 detects spontaneous flow without monitoring an amplitude of blood flow (e.g., a magnitude of blood velocity, volumetric blood flow, or volume through the blood vessel). Because spontaneous circulation results in a minimal amount retrograde flow, the flow monitor 106 may detect spontaneous circulation by detecting an amount of time that the flow in the blood vessel is retrograde flow. If the amount of time (e.g., a percentage of a predetermined time period, such as a 30 second time period) that retrograde flow is detected is below a threshold, the flow monitor 106 may infer that spontaneous circulation is present.

In some cases, the flow monitor 106 is configured to detect spontaneous circulation based on an analysis of both blood flow in a blood vessel (e.g., the artery 108 or the vein 110) and an electrocardiogram (ECG) of the subject 102. In some cases in which the subject 102 is receiving chest compressions from the mechanical chest compression device 104 while the ECG is being detected (e.g., via electrodes placed on the chest of the subject 102), the ECG may include a chest compression artifact. The chest compression artifact can be removed or reduced, for instance, by applying a comb filter to the ECG. In some cases, the comb filter is applied by the flow monitor 106, or by an external monitor (not illustrated) that is detecting the ECG. In various implementations, the flow monitor 106 detects times at which a characteristic (e.g., a QRS complex) is present in the ECG. Further, the flow monitor 106 detects times at which local maxima of a flow parameter (e.g., blood velocity, volumetric flow rate, etc.) are observed. Notably, the farther that the blood vessel is located from the heart of the subject 102, the longer it would take the spontaneously beating heart of the subject 102 to push blood through the blood vessel. Thus, spontaneous circulation may be present if the local maxima of the flow parameter occur after the characteristic is detected in the ECG by a consistent time interval. For instance, the flow monitor 106 may detect spontaneous circulation by detecting that greater than a threshold number of ECG characteristic-blood flow maxima pairs are within a threshold time delay (e.g., 50 ms) of one another.

The following Table 1 summarizes various techniques that the flow monitor 106 may utilize for detecting spontaneous circulation, or a lack of spontaneous circulation, in the subject 102 when the subject 102 is not receiving chest compressions. Notably, some of these techniques enable the flow monitor 106 to detect spontaneous circulation, or the lack of spontaneous circulation, by monitoring a single blood vessel (e.g., either the artery 108 or the vein 110). In some implementations, these techniques can be combined.

TABLE 1

Techniques for monitoring blood flow when chest compressions are not administered

| | Monitoring Artery | Monitoring Vein |
|---|---|---|
| Spontaneous Circulation (e.g., normal sinus rhythm) | Net displaced volume through cross-section during time period (e.g., cardiac cycle) in direction away from the heart is above a threshold | Net displaced volume through cross-section during time period (e.g., cardiac cycle) in direction toward the heart is above a threshold |
| | Average flow rate away from the heart over the time period is above a threshold | Average flow rate toward the heart over the time period is above a threshold |
| | Velocity and/or flow rate (away from the heart and with respect to time) waveform is pulsatile, with peak amplitude above a threshold | Velocity and/or flow rate (toward the heart and with respect to time) waveform is substantially constant with a mean above a threshold |
| Lack of Spontaneous Circulation (e.g., VF or asystole) | Net displaced volume through cross-section during time period in direction away from the heart is below a threshold | Net displaced volume through cross-section during time period in direction toward the heart is below a threshold |
| | Velocity and/or flow rate (away from the heart and with respect to time) waveform is substantially constant with a peak amplitude below a threshold | Velocity and/or flow rate (toward the heart and with respect to time) waveform is substantially constant with a mean (sampled during a time period) below a threshold |

The following Table 2 summarizes various techniques that the flow monitor 106 may utilize for detecting spontaneous circulation, or a lack of spontaneous circulation, in the subject 102 when the subject 102 is receiving chest compressions. Notably, some of these techniques enable the flow monitor 106 to detect spontaneous circulation, or the lack of spontaneous circulation, by monitoring a single blood vessel (e.g., either the artery 108 or the vein 110). In some implementations, these techniques can be combined. For instance, the flow monitor 106 may detect spontaneous circulation by determining that a ratio of an arterial peak blood velocity or blood flow away from the heart to a venous peak velocity or blood flow toward the heart is greater than a threshold. In some cases, the flow monitor 106 may detect a lack of spontaneous circulation by determining that the ratio is less than a threshold.

TABLE 2

Techniques for monitoring blood flow when chest compressions are administered

| | Monitoring Artery | Monitoring Vein |
|---|---|---|
| Spontaneous Circulation (e.g., normal sinus rhythm) | Net displaced volume through cross-section during time period (e.g., cardiac cycle) in direction away from the heart is above a threshold | Net displaced volume through cross-section during time period (e.g., cardiac cycle) in direction toward the heart is above a threshold |

TABLE 2-continued

Techniques for monitoring blood flow when chest compressions are administered

| | Monitoring Artery | Monitoring Vein |
|---|---|---|
| | Velocity and/or flow rate (away from the heart and with respect to time) waveform is pulsatile, with peak amplitude above a threshold | Velocity and/or flow rate (toward the heart and with respect to time) waveform is pulsatile |
| Lack of Spontaneous Circulation (e.g., VF or asystole) | Net displaced volume through cross-section during time period in direction away from the heart is below a threshold | Net displaced volume through cross-section during time period in direction toward the heart is below a threshold |
| | | Velocity and/or flow rate (toward the heart and with respect to time) waveform is pulsatile with a mean (sampled during a time period) below a threshold |

According to some cases, the flow monitor 106 outputs a communication signal indicating one or more flow parameters 120 to an output device 122. The flow parameter(s) 120, for instance, include the presence or absence of blood flow through the artery 108, the presence or absence of blood flow through the vein 110, the direction of blood flow through the artery 108, the direction of blood flow through the vein 110, the velocity of blood flow through the artery 108, the velocity of blood flow through the vein 110, the flow rate of blood through the artery 108, the flow rate of blood through the vein 110, the vein volume 116, the artery volume 118, any other flow-related metric described herein (e.g., one or more ratios of the aforementioned metrics), or any combination thereof.

The output device 122, in various examples, is configured to output an indication of the flow parameter(s) 120 to a user (e.g., a rescuer). The output device 122, in various examples, may be a computing device, a mobile device (e.g., a mobile phone, tablet computer, etc.), a monitor (e.g., a subject monitor), a medical device (e.g., a monitor-defibrillator), or any combination thereof. In some examples, the output device 122 includes a display (e.g., a screen) that is configured to visually present the flow parameter(s) 120. In some cases, the output device 122 includes a speaker configured to audibly present the flow parameter(s) 120.

In some implementations, the output device 122 generates an alarm based on the flow parameter(s) 120. For example, the output device 122 may output the alarm in response to determining that the flow parameter(s) 120 are above a first threshold or below a second threshold. In some cases, the alarm is visually presented (e.g., a blinking light, a flashing pop-up on a screen, or some other graphical user interface (GUI) element) or audibly presented (e.g., a shrill sound, beeping, or other sound designed to catch the attention of a user). Accordingly, the output device 122 may alert a user (e.g., a rescuer) to sudden deteriorations in the condition of the subject 102 due to blood flow.

In various examples, the flow monitor 106 analyzes the flow parameter(s) 120 and outputs an instruction 124 to the mechanical chest compression device 104 based on the analysis. For example, the flow monitor 106 may determine that the chest compressions administered by the mechanical chest compression device 104 are ineffective. In response to determining that the chest compressions are ineffective, the instruction 124 may direct the mechanical chest compression device 104 to alter one or more chest compression parameters. For example, the instruction 124 may direct the mechanical chest compression device 104 to change a position on the chest of the subject 102 to which the chest compressions are being applied by the mechanical chest compression device 104, a rate of the chest compressions, a speed of the chest compressions (e.g., a speed of a plunger used to administer the chest compressions), a duty cycle of the chest compressions (e.g., a fraction of time that the plunger is in compressing and/or in contact with the chest of the subject 102 during a chest compression cycle), a compression depth of the chest compressions (e.g., a distance between the lowest location of the plunger during a chest compression and a height of the chest of the subject 102 between chest compressions), a height of recoil of the chest compressions (e.g., a distance between the highest location of the plunger between chest compressions and the height of the chest of the subject 102 between chest compressions), or any combination thereof. In some examples, the flow monitor 106 may generate the instruction 124 to direct the mechanical chest compression device 104 to pause or refrain from administering chest compressions in response to determining that blood is spontaneously circulating in the body of the subject 102. The mechanical chest compression device 104, in some cases, initiates, halts, or modifies the chest compressions based on the instruction 124.

Although FIG. 1 has been described with respect to chest compressions administered by the mechanical chest compression device 104, implementations are not so limited. In some cases, various implementations of the present disclosure can monitor and/or provide feedback regarding manual chest compressions administered by a rescuer. For example, the flow monitor 106 may output an indication that chest compressions are ineffective, a recommendation to change a chest compression parameter, an indication that blood is spontaneously circulating in the subject 102, or a recommendation to cease administering chest compressions to the subject 102.

Although FIG. 1 illustrates the mechanical chest compression device 104, the flow monitor 106, and the output device 122 as separate devices, implementations are not so limited. For example, any combination of the mechanical chest compression device 104, the flow monitor 106, and the output device 122 can be integrated into a single device. Furthermore, in some examples, the flow monitor 106 is integrated with, or communicatively coupled to, additional devices. For example, the flow monitor 106 may be integrated within, or coupled to, a monitor-defibrillator that is configured to monitor and/or treat the subject 102.

A specific example will now be described with respect to FIG. 1. In this example, the subject 102 has collapsed suddenly from cardiac arrest in a non-clinical setting, such as an airport terminal. A rescuer (not illustrated) has come to the aid of the subject 102. After manually detecting a lack of a pulse of the subject 102 (e.g., by holding fingers to the wrist of the subject 102), the rescuer applies the mechanical chest compression device 104 to the body of the subject 102. The rescuer activates the mechanical chest compression device 104, causing it to administer chest compressions to the subject 102. In addition, the rescuer has applied the flow monitor 106 to an upper leg of the subject 102. The flow monitor 106 wirelessly pairs to the mechanical chest compression device 104 via a BLUETOOTH™ channel. In addition, the flow monitor 106 wirelessly pairs with the output device 122, which may be a smart phone of the rescuer.

In this example, the flow monitor 106 determines a peak flow rate of blood flowing through the artery 108 and determines that the peak flow rate is below a predetermined threshold. In addition, the flow monitor 106 determines that a peak flow rate of blood flowing through the vein 110 is below a predetermined threshold. Accordingly, the flow monitor 106 determines that the chest compressions administered by the mechanical chest compression device 104 are ineffective. In various cases, the flow monitor 106 outputs the instruction 124 to direct the mechanical chest compression device 104 to change a chest compression parameter of the chest compressions. For instance, the flow monitor 106 instructs the mechanical chest compression device 104 to increase a compression depth and/or move a position of the chest compressions in a direction toward a center of the chest of the subject 102. In some cases, the flow monitor 106 confirms that the chest compressions become effective after the mechanical chest compression device changes the chest compression parameter.

Eventually, the subject 102 recovers from cardiac arrest while the chest compressions are being administered. The heart of the subject 102 initiates spontaneous circulation of blood in the body of the subject 102. The flow monitor 106 detects the ROSC by determining that a ratio of anterograde flow to retrograde flow in the artery 108 or vein 110 is greater than a threshold. Upon detecting ROSC, the flow monitor 106 outputs another instruction 124 that directs the mechanical chest compression device 104 to pause the chest compressions.

In some implementations, the flow monitor 106 outputs an image indicative of the blood flowing through the artery 108 and the blood flowing through the vein 110. For instance, the flow monitor 106 may include a screen (or other type of display) configured to visually present the image, or may transmit data indicative of the image to an external device configured to visually present the image. In some cases, the image includes a cross-sectional image of the artery 108 and a cross-sectional image of the vein 110. Detected flow through the artery 108 and the vein 110, for instance, can be represented by colors presented within the cross-sectional images. In some cases, flow from spontaneous circulation is displayed in a first color and chest-compression-induced flow is displayed in a second color, wherein the first color is different than the second color.

In some cases, the image includes one or more waveforms. For example, the image may include overlaid waveforms representing flow through the artery 108 and flow through the vein 110 with respect to time during the same event. In some examples, the image includes overlaid waveforms representing flow through the artery 108, or flow through the vein 110, in different time intervals representing successive instances of the same type of event (e.g., successive heartbeats, chest compressions, or the like). In some examples, a shape is overlaid on the waveforms indicating the occurrence of an event, such as a chest compression administered to the subject 102.

Alternatively or in addition, the flow monitor 106 outputs one or more audio signals indicative of the data indicated by the waveform(s). For example, the flow monitor 106 includes a speaker that outputs one or more audio channels. Different audio channels, for instance, can be represented as sounds from different speakers and/or different locations on the flow monitor 106. In some cases, different audio channels are represented as different types of sounds (e.g., sounds having different frequencies), which may be output by a single speaker. In some cases, one set of data is output via a first audio channel and a second set of data is output via a second audio channel.

FIGS. 2A and 2B illustrate waveforms of blood flow through veins and arteries with respect to time. For example, the waveforms illustrated in FIGS. 2A and 2B can be generated by, or based on data generated by, a flow monitor (e.g., the flow monitor 106 described above with reference to FIG. 1). In both FIGS. 2A and 2B, a horizontal axis represents time and a vertical axis represents blood flow. Blood flow, for instance, may represent a velocity of blood through a blood vessel (e.g., a peak or mean velocity through a cross-section of the blood vessel), a flow rate, a net flow of blood, or any other indicator of blood flow through the blood vessel. Solid lines represent flow through an example artery. Dashed lines represent flow through an example vein. Solid and dashed line waveforms appearing on the same axis are aligned. In some cases, the waveforms illustrated in FIGS. 2A and 2B are output by the flow monitor and/or an external device that is communicatively coupled with the flow monitor.

FIG. 2A illustrates waveforms of blood spontaneously flowing through an example artery and an example vein with respect to time. The solid-line waveform represents arterial flow 200 in an anterograde direction. The dashed-line waveform represents venous flow 202 in an anterograde direction. The dotted line represents a flow equal to zero. As illustrated, the shapes of the arterial flow 200 and venous flow 202 waveforms are different during spontaneous circulation. Namely, an arterial peak 204 of the arterial flow waveform 200 is significantly larger than a venous peak 206 of the venous flow 202 waveform. Accordingly, a flow monitor may determine that the arterial flow 200 and venous flow 202 are indicative of spontaneous circulation by determining that a ratio of the arterial peak 204 to the venous peak 206 is above a threshold.

FIG. 2B illustrates waveforms of blood flowing through an example artery an example vein with respect to time due to the application of chest compressions. The solid-line waveform represents arterial flow 208. The dashed-line waveform represents venous flow 210. The dotted line represents a flow equal to zero. When the waveforms are above the dotted line, they are representative of anterograde flow. When the waveforms are below the dotted line, they are representative of retrograde flow. As illustrated, the shapes of the arterial flow 208 and the venous flow 210 are similar during chest compressions. For instance, an arterial peak 212 of the arterial flow 208 and a venous peak 214 of the venous flow 210 are similar. Accordingly, a flow monitor may determine that the arterial flow 208 and the venous flow 210 are indicative of (effective) chest compressions without spontaneous circulation by determining that a ratio of the arterial peak 212 to the venous peak 214 is below a threshold.

FIG. 3 illustrates an example GUI element 300 that portrays a changing condition of a subject over multiple cycles of an event. In various cases, the GUI element 300 displays a first waveform 302 and a second waveform 304. The first waveform 302 represents an amount of blood flow to a physiological structure (e.g., the brain) of a subject during a first instance of the event. The second waveform 304 represents an amount of blood flow to the physiological structure during a second instance of the event. In some cases, the second instance of the event occurs immediately after the first instance of the event. In some examples, one or more additional instances of the event occur between the first instance and the second instance.

Various types of events can be portrayed using the GUI element 300. For example, the event could be a CPR cycle (e.g., any combination of chest compressions and/or rescue breaths or ventilation cycles), a chest compression cycle (e.g., including a compression phase and a release/recoil phase), a ventilation cycle (e.g., a positive pressure ventilation (PPV) cycle), a cardiac cycle (e.g., diastole and systole, just diastole, just systole, or the like), or any combination thereof. The occurrence of the event can be detected using various techniques. In some cases, the entity outputting the GUI element 300 (e.g., a medical device outputting the GUI element 300) receives a communication signal from an external device indicating a timing of the event. For example, a mechanical chest compression device may indicate the timing of a chest compression it is administering, a ventilation device may output an indication of a PPV event it is administering, or the like. In some examples, the entity detects the event using one or more sensors. For example, the entity may detect the administration of a chest compression using a pressure sensor disposed on the chest of the subject or by detecting a chest compression artifact in an ECG or transthoracic impedance of the subject. In some implementations, the entity detects a ventilation cycle by detecting one or more airway parameters of the subject (e.g., a partial pressure of $CO_2$ in the airway of the subject) or by detecting a ventilation artifact in the ECG or transthoracic impedance. In some examples, the entity detects a cardiac cycle by detecting the presence of a QRS complex in the ECG and/or by detecting blood flow indicative of systole and diastole using a flow monitor.

The first waveform 302 and the second waveform 304 are displayed with respect to the same axes. A horizontal axis represents an amount of time during a given event cycle. A vertical axis represents an amount of blood flow to the physiological structure. In various cases, blood flow can represent blood velocity, flow rate, volume, or any other parameter that is indicative of blood flow. For instance, the amount of blood flow to the physiological structure may be representative of a net flow volume of blood to the structure.

The GUI element 300, in various examples, illustrates a changing condition of a subject. For example, in an example in which the first waveform 302 represents a flow rate through a vein of the subject during a first cardiac cycle and the second waveform 304 represents a flow rate through the vein of the subject during a second cardiac cycle, the GUI element 300 may illustrate, to a rescuer, that the heart of the subject is becoming less effective at pumping blood over time. Thus, the rescuer may proactively prepare to administer chest compressions to the subject based on the degrading condition of the heart.

In various implementations, the GUI element 300 may portray, to a rescuer, an ongoing efficacy of a treatment. For instance, in an example in which the first waveform 302 represents a flow rate through an artery of the subject during a first chest compression cycle and the second waveform 304 represents a flow rate through the vein of the subject during a second chest compression cycle, the GUI element 300 may illustrate, to the user, that the chest compressions are becoming less effective over time. In some cases, the GUI element 300 may prompt the rescuer to check whether a mechanical chest compression device administering the chest compressions has changed a chest compression position away from a center of the subject's chest, and may reposition the mechanical chest compression device accordingly.

In some examples, the GUI element 300 is enhanced or substituted for one or more other representations of the parameter. For example, the entity may audibly output an indication of the first waveform 302 and the second waveform 304. For instance, the entity outputs data indicative of the first waveform 302 in a first audio channel (e.g., a first pitch) and data indicative of the second waveform 304 in a second audio channel (e.g., a second pitch). In some cases, the entity outputs a numeric and/or text indicator of a condition of the subject.

Figure 4:
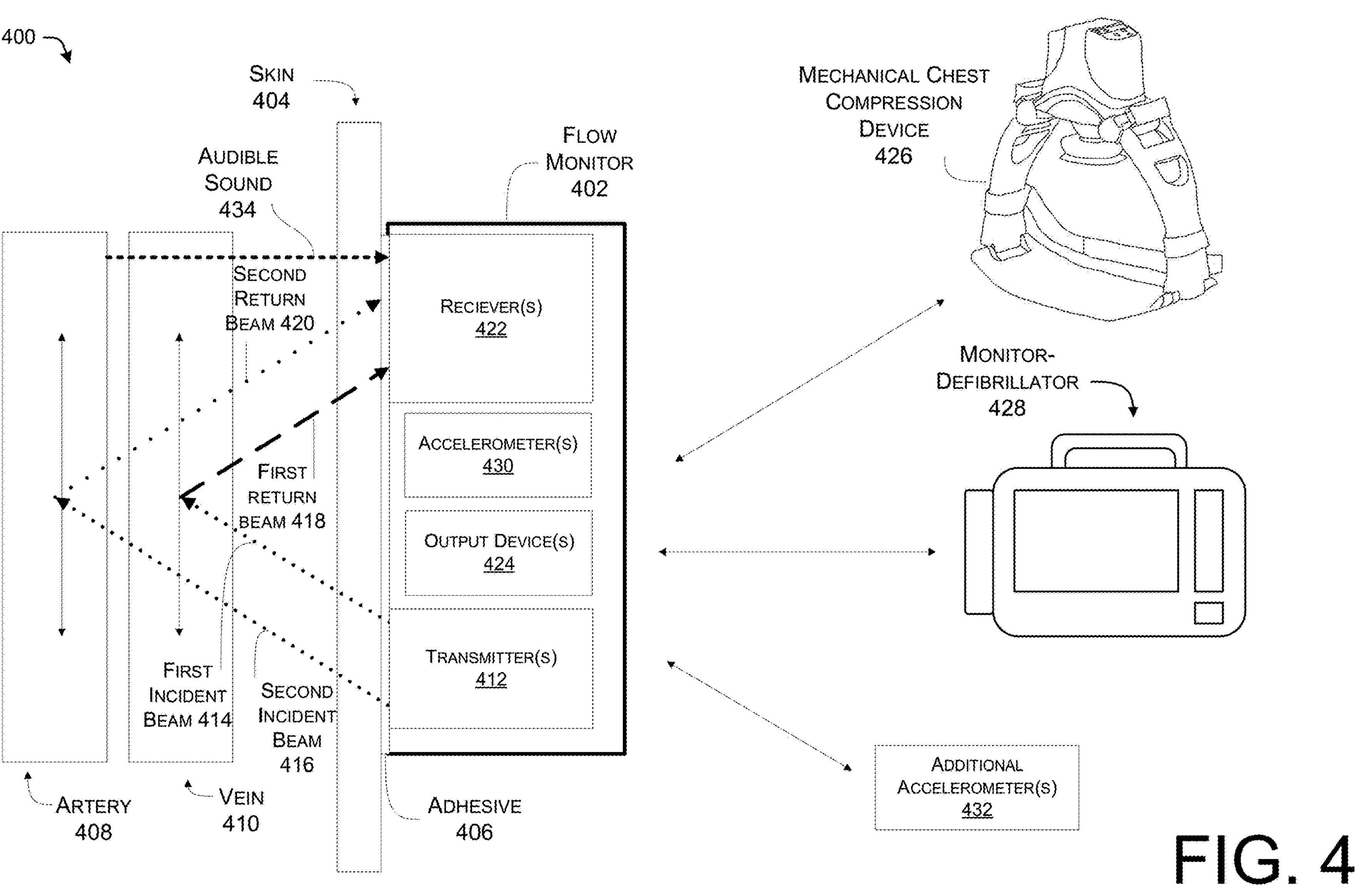
FIG. 4 illustrates an example environment for monitoring blood flow through one or more blood vessels of a subject.

FIG. 4 illustrates an example environment 400 for monitoring blood flow through one or more blood vessels of a subject. A flow monitor 402 is adhered to skin 404 of the subject via an adhesive 406. In some examples, the flow monitor 402 is the flow monitor 106 described above with reference to FIG. 1. The flow monitor 402, for instance, is located outside of the body of the subject. In some implementations, the flow monitor 402 is held on the skin 404 by a strap, a buckle, a bandage, or some other fastener. For instance, the flow monitor 402 may be wrapped around an extremity of the subject.

In various implementations, an artery 408 and a vein 410 are disposed underneath the skin 404. The artery 408 and the vein 410 are part of the circulatory system of the subject. The circulatory system includes a fluid circuit of various blood vessels (including the artery 408 and the vein 410). The subject includes a heart that, when functioning, pumps blood through the blood vessels. In particular, the heart moves blood from lungs of the subject, where the blood can be oxygenated, to other portions of the subject's body, such as the brain, other organs, and the subject's extremities. Along the circulatory system, cells within the blood deliver oxygen to cells of the subject, thereby supporting cellular respiration. In various cases, the artery 408 carries oxygenated blood from the lungs of the subject and the vein 410 carries deoxygenated blood toward the lungs. Examples of the artery 408 include a carotid artery, a subclavian artery, a coronary artery, a brachial artery, an iliac artery, a radial artery, a femoral artery, or a pulmonary artery. Examples of the vein 410 include a jugular vein, an iliac vein, a subclavian vein, a cephalic vein, a brachial vein, a basilic vein, a hepatic vein, a radial vein, an ulnar vein, a digital vein, a brachiocephalic vein, a femoral vein, a saphenous vein, a venous arch, or a tibial vein. In some cases, the pulmonary artery carries deoxygenated blood.

According to various implementations of the present disclosure, the flow monitor 402 is configured to detect the flow of blood through the artery 408 and/or vein 410. In particular cases, the flow monitor 402 includes one or more transmitters 412 configured to output one or more incident beams toward the artery 408 and/or vein 410. In the example illustrated in FIG. 4, the incident beams include a first incident beam 414 and a second incident beam 416.

In various cases, the first incident beam 414 and the second incident beam 416 include waves that are transmitted through the skin 404. The waves, for example, can be instantiated as light and/or sound. In various cases, the first incident beam 414 and the second incident beam 416 include at least one of infrared, near-infrared, or visible light. For instance, the light may have a frequency in a range of 300 GHz-430 THz and a wavelength in a range of 700 nanometers (nm) to 1 millimeter (mm). For instance, the transmitter(s) 412 include one or more light sources, such as light-emitting diodes (LEDs) or lasers. In some examples, the transmitter(s) 412 may include one or more mirrors configured to split the light output by the light source(s), such as for an interferometric analysis. In some cases, the receiver(s) 422 include one or more light sensors, such as at least one of a photodiode, a phototransistor, a photomultiplier tube, a charge-coupled device, a metal-semiconductor-metal photodetector, or a complementary metal oxide semiconductor photodetector.

According to various implementations, the waves include ultrasound. As used herein, the term "ultrasound," and its equivalents, can refer to mechanical waves (e.g., in the form of pressure waves) having a frequency in a range of 20 kilohertz (kHz) to 200 megahertz (MHz). Ultrasound, for example, is sound in a frequency that is greater than an upper detection limit of a human ear. In various instances, transmitter(s) 412 include one or more piezoelectric crystals (including, e.g., lead zirconate titanate (PZT), $LiNbO_3$ (LN), lead magnesium niobate-lead titanate (PMN-PT), or lead indium niobate-lead magnesium niobate-lead titanate (PIN-PMN-PT)). When an electrical current is induced through the piezoelectric crystal(s), the piezoelectric crystal(s) vibrate at a frequency that produces ultrasound. In some examples, the transmitter(s) 412 include one or more microelectromechanical system (MEMS) devices. In some instances, the transmitter(s) 412 include one or more capacitive micromachined ultrasonic transducers (CMUTs) and/or piezoelectric micromachined ultrasonic transducers (PMUT). Any electrical to mechanical conversion system or material that operates at the ultrasound frequency range would be suitable.

According to various implementations, the flow monitor 402 includes one or more ultrasound transducers. As used herein, the terms "ultrasound transducer," "ultrasonic transducer," "transducer," and their equivalents, may refer to a device that generates or detects ultrasound. For instance, the ultrasound transducer(s) include the transmitter(s) 412 and/or the receiver(s) 422. In some cases, an ultrasound transducer includes a transducer element (e.g., a piezoelectric crystal, MEMS device, or another type of electrical-to-mechanical conversion device), a first electrode disposed on one side of the transducer element, and a second electrode disposed on another side of the transducer element. In various implementations, the ultrasound transducer is configured to produce ultrasound by inducing a current through or a voltage between the first and second electrodes. In some cases, the ultrasound transducer is configured to detect ultrasound by detecting a current through or voltage between the first and second electrodes that is induced when the ultrasound is received by the transducer element. In some cases, the ultrasound transducer is encased in a housing, which may be watertight. The ultrasound transducer, in some examples, further includes a matching layer that is disposed between the transducer element and a surface of the housing from which an incident beam of ultrasound is emitted. The matching layer includes a material having an acoustic impedance that is between the acoustic impedance of the transducer element and an acoustic lens (if one exists or between the transducer and skin). In some implementations, a gel layer is disposed between the housing of the ultrasound transducer and the skin 404 that further matches the impedance between the ultrasound transducer and the body, thereby preventing the first incident beam 414 and the second incident beam 416 from being reflected by an interface containing air between the skin 404 and the ultrasound transducer. In some cases, the adhesive 406 serves as the gel layer.

In some examples, the first incident beam 414 is reflected and/or scattered by blood in the vein 410, thereby generating a first return beam 418. Further, in some cases, the second incident beam 416 is reflected and/or scattered by blood in the artery 408, thereby generating a second return beam 420. The flow monitor 402 includes one or more receivers 422 configured to detect the first return beam 418 and/or the second return beam 420.

As illustrated, the artery 408 and the vein 410 are substantially parallel to the skin 404. In various implementations of the present disclosure, the transmitter(s) 412 emit the first incident beam 414 and/or the second incident beam 416 in a direction that is non-perpendicular and non-parallel to the surface of the flow monitor 402 that is adhered to the skin 404. That is, the transmitter(s) 412 emit the first incident beam 414 and/or the second incident beam 416 in an angled fashion. Thus, a component of the first incident beam 414 is parallel to the blood flow through the vein 410 and/or a component of the second incident beam 416 is parallel to the blood flow through the artery 408.

Various implementations of the transmitter(s) 412 that enable angled transmission of the first incident beam 414 and the second incident beam 416 are disclosed herein. In some implementations in which the transmitter(s) 412 include one or more transducer elements configured to emit ultrasound, an individual transducer element may have the shape of a cylinder (with a height of the cylinder being substantially parallel to the skin 404 and perpendicular to a direction of the artery 408 and/or vein 410) or a polygonal prism (with a height of the polygonal prism being substantially parallel to the skin 404 and perpendicular to a direction of the artery 408 and/or vein 410). In some cases, a piezoelectric crystal may be divided into sections defined by an angle perpendicular to the height of the cylinder, each section serving as a different transducer element configured to emit ultrasound. In some cases, the transmitter(s) 412 include multiple (e.g., planar) transducer elements that emit respective ultrasound beams that are phase networked together such that they collectively form the angled first incident beam 414 or the second incident beam 416. In some cases, the transmitter(s) 412 include a single transducer element including portions that are insensitive to ultrasound (e.g., non-piezoelectric portions, such as including a polymer) and portions that are sensitive to ultrasound (e.g., piezoelectric portions), which can cause the first incident beam 414 or the second incident beam 416 to be output as a grating lobe. The grating lobe may include components emitted at different angles, at least one of which may include the first incident beam 414 or the second incident beam 416 to be transmitted at an angle with respect to the artery 408 or vein 410.

In some implementations, the transmitter(s) 412 include a transducer element that emits ultrasound from a surface that is nonparallel to the skin 404. For example, the flow monitor 402, in some cases, includes a wedge-shaped spacer between the crystal and the skin 404. The spacer may be substantially acoustically transparent. In some examples, the wedge-shaped spacer includes a polymer or gel that is configured to perform impedance matching between the crystal and the skin 404. For instance, the spacer may include multiple layers arranged in steps that are configured to be in contact with the crystal and/or tilt the crystal with respect to the skin 404.

In some cases, the flow monitor 402 includes an acoustic "lens" that is disposed between a crystal emitting ultrasound and the skin 404. For example, the acoustic lens can be a spacer with a nonuniform acoustic impedance. Thus, the acoustic lens may bend the ultrasound emitted by the crystal before it is transmitted through the skin 404.

In some examples, the transmitter(s) 412 includes a crystal that is disposed inside of a needle that is disposed through the skin 404. In some implementations, the transmitter(s) 412 include an array of crystals configured to emit the first incident beam 414 and/or the second incident beam 416 through the skin 404. For example, the array may be arranged on a curved surface, such that individual crystals may point in different directions. In operation, the flow monitor 402 may automatically determine which incident beams whose return beams produce a greatest frequency and/or phase shift with respect to the incident beams, and may define those beams as the first incident beam 414 and/or the second incident beam 416.

In various implementations, the first return beam 418 may represent a frequency and/or phase shift with respect to the first incident beam 414 due to the Doppler effect. Similarly, because the component of the second incident beam 416 is parallel to the blood flow through the artery 408, the second return beam 420 may represent a frequency and/or phase shift with respect to the second incident beam 416 due to the Doppler effect. These shifts occur due to the Doppler effect and may be referred to as "Doppler shifts."

According to various implementations, the flow monitor 402 determines a velocity of the blood flow through the artery 408 and the vein 410 due to a difference between the frequencies of the first incident beam 414 and the first return beam 418, as well as a difference between the frequencies of the second incident beam 416 and the second return beam 420. The transmitter(s) 412, in some cases, operate in a continuous wave Doppler mode (also referred to as "CW Doppler"), and continuously transmit the first incident beam 414 and the second incident beam 416 during a monitoring period. The receiver(s) 422, for instance, continuously detect the first return beam 418 and the second return beam 420 during the monitoring period. For instance, the flow monitor 402 detects the blood velocity in the artery 408 and the blood velocity in the vein 410, in-real time, continuously or semi-continuously based on the frequency shifts between the first incident beam 414 and the first return beam 418 as well as between the second incident beam 416 and the second return beam 420.

In various implementations, the flow monitor 402 operates in a pulsed-wave Doppler mode (also referred to as "PW Doppler"). For instance, the flow monitor 402 causes the incident beam 416 to output the first incident beam 414 and/or the second incident beam 416 in pulses and detects the first return beam 418 and/or the second return beam 420 as return pulses. In various cases, a time delay between the output pulses and the return pulses is indicative of the depth of a structure from which the return pulses are reflected. In various implementations, the flow monitor 402 can determine the blood velocity in the artery 408 based on phase shifts between the pulses of the first incident beam 414 and the first return beam 418. Further, the flow monitor 402 can determine the blood velocity in the vein 410 based on phase shifts between the pulses of the second incident beam 416 and the second return beam 420.

In some cases, the flow monitor 402 detects the blood velocities at a sampling rate that corresponds to at least twice the component of the velocity range in the direction of the beam pointing angle of the first incident beam 414 and/or the second incident beam 416.

In some examples, the flow monitor 402 performs laser Doppler velocimetry in order to detect the blood velocity. In various cases, the flow monitor 402 includes one or more interferometric sensors. For example, the first incident beam 414 and the second incident beam 416 are light beams (e.g., coherent light beams) that are split (e.g., by one or more mirrors) prior to transmission through the skin 404. The flow monitor 402 may detect the blood velocities in the artery 108 and the vein 410 by comparing the first return beam 418 and the second return beam 420 to the split beams generated from the first incident beam 414 and the second incident beam 416. Techniques for interferometric detection of blood velocity can be found in, for example, R. D. Rader, C. M. Stevens and J. P. Meehan, "An Interferometric Blood Flow Measurement Technique—A Brief Analysis," in IEEE Transactions on Biomedical Engineering, vol. BME-21, no. 4, pp. 293-297, July 1974; Nagahara, et al., Method. Invest. Ophthalmol. Vis. Sci. 2011; 52(1):87-92; and Robinson, et al., Sci Rep 13, 8803 (2023), each of which is incorporated by reference herein in its entirety.

In some cases, the flow monitor 402 images a portion of the subject that includes the artery 408 and the vein 410. In some cases, the flow monitor 402 generates an image using the first return beam 418 and the second return beam 420 using one or more sonographic techniques. In various implementations, the flow monitor 402 generates the image using multiple return beams including the first return beam 418 and the second return beam 420. The flow monitor 402, in some implementations, generates the multiple return beams by sweeping the first incident beam 414 and the second incident beam 416 across a section of the subject being imaged. For example, the flow monitor 402 may generate a real-time image of the subject that includes cross-sections of the artery 408 and vein 410, respectively. In some implementations, the flow monitor 402 automatically segments the cross-sections of the artery 408 and vein 410 in the real-time image. In some cases, the flow monitor 402 performs segmentation of a scrolling Doppler image (e.g., Doppler shift in a y-axis is swept in time along an x-axis) to segregate out the Doppler information of the vein 410 from the artery 408. Various types of segmentation techniques can be used, such as detection using histogram of oriented gradients (HOG) features, a scale-invariant feature transform (SIFT), Viola-Jones object detection framework, or You Only Look Once (YOLO). Once the cross-sections depicted in the image are identified using image segmentation, the flow monitor 402 can further classify the cross-sections using a support vector machine (SVM). In some cases, the flow monitor 402 uses one or more trained convolutional neural networks (CNNs) to segment and/or classify the cross-sections of the artery 408 and the vein 410 depicted in the image. In various cases, the flow monitor 402 may differentiate the cross-section corresponding to the artery 408 an the cross-section corresponding to the vein 410.

In particular implementations, the flow monitor 402 detects the velocity of the blood through the artery 408 and the velocity of the blood through the vein 410, simultaneously. For example, the first return beam 418 may be reflected from the artery 408 and the second return beam 420 may be reflected from the vein 410, so that the flow monitor 402 can detect the blood velocity of the artery 408 based on the first return beam 418 and may detect the blood velocity of the vein 410 based on the second return beam 420.

Simultaneously monitoring the blood velocity through the artery 408 and the vein 410 may enable certain evaluations of the subject. In some implementations, the flow monitor 402 detects a volumetric flow rate or net flow volume (e.g., during a time period) through at least a portion of the subject based on the blood velocity through the artery 408 and the vein 410. In some cases, the flow monitor 402 determines the volumetric flow rate through the artery 408 by integrating the velocity of the blood through the artery 408 across a cross-sectional area of the artery 408. The flow monitor 402 may determine the volumetric flow rate through the vein 410 by integrating the velocity of the blood through the vein 410 across a cross-sectional area of the vein 410. In various implementations, the flow monitor 402 is configured to detect a net flow volume that flows through the cross-section of the artery 408 during a time period (e.g., a cardiac cycle, a chest compression cycle, a portion of a chest compression cycle, or any combination thereof) by integrating the volumetric flow rate through the artery 408 over the time period. Similarly, the flow monitor 402 is configured to detect a net flow volume that flows through the cross-section of the vein 410 during the time period by integrating the volumetric flow rate through the vein 410 over the time period.

The artery 408, for instance, supplies oxygenated blood to the portion of the subject, and the vein 410 transports deoxygenated blood from the portion of the subject. In some examples, the flow monitor 402 is configured to detect a net flow volume of blood to a portion of the subject's body over time. In particular cases, the artery 408 is a carotid artery and the vein 410 is a jugular vein, and the flow monitor 402 is configured to detect a net flow volume of blood to the brain of the subject over time.

The flow monitor 402 may assess a condition of the subject and/or evaluate a treatment administered to the subject by analyzing blood flow parameters (e.g., velocity, volumetric flow rate, or net flow volume of blood) in the artery 408 and/or the vein 410. In some implementations, the flow monitor 402 identifies chest compressions performed on the subject based on the blood velocity through the artery 408 and/or the blood velocity through the vein 410. When (e.g., effective) chest compressions are performed on the subject, the compressions push blood through the artery 408 and the vein 410 in a direction that moves distally from the chest. Thus, chest compressions cause blood flowing through the artery 408 and blood flowing through the vein 410 to travel in parallel directions. Moreover, an individual chest compression causes the blood to flow in the artery 408 and vein 410 in a surge. Thus, in some cases, the flow monitor 402 detects that chest compressions are being performed on the subject by detecting that the blood through the artery 408 and the blood through the vein 410 is traveling in the same or parallel directions (e.g., in a direction pointing distally from the chest). For instance, the flow monitor 402 can detect whether chest compressions are undesirably moving blood in the same direction through the artery 408 and the vein 410.

In some cases, the flow monitor 402 provides feedback about the efficacy of the chest compressions based on the blood velocity through the artery 408 and the vein 410 and/or the net flow volume to the portion of the subject. For instance, if the flow monitor 402 detects less than a threshold blood velocity through the artery 408 or vein 410, or detects less than a threshold net flow volume to the portion of the subject (e.g., during a particular time period), the flow monitor 402 can output a feedback signal via one or more output devices 424. The output device(s) 424, for instance, include a display (e.g., a screen configured to visually output signals), a speaker (e.g., configured to audibly output signals), a haptic feedback device (e.g., configured to convey signals by vibrating or otherwise moving), a transceiver (e.g., configured to transmit signals to external devices), or any combination thereof. In some cases, the feedback signal is output to a rescuer (not illustrated) performing the chest compressions, and may cause the rescuer to adjust the depth of the chest compressions, adjust the frequency of the chest compressions, or adjust the position of the chest compressions relative to the subject's chest.

In some implementations, the feedback signal is transmitted to a mechanical chest compression device 426 that is performing the chest compressions. The mechanical chest compression device 426, in some cases, administers the chest compressions by moving a plunger up and down on the subject's chest. The feedback signal, for instance, causes the mechanical chest compression device 426 to adjust the depth of the chest compressions, adjust the frequency of the chest compressions, adjust the position of the plunger relative to the subject's chest, pause chest compressions, or initiate chest compressions. In some implementations, the mechanical chest compression device 426 transmits a signal to the flow monitor 402 that indicates the timing, frequency, position, or another chest compression parameter characterizing the chest compressions administered by the mechanical chest compression device 426. The flow monitor 402, in some cases, generates the feedback signal based on the chest compression parameter, such that the feedback signal is specific to the conditions reported by the mechanical chest compression device 426.

The placement of chest compressions, in particular, impacts the flow of blood through specific blood vessels through the subject's body. In some cases, the flow monitor 402 enables optimization of the position of the chest compressions based on the flow rate through the artery 408, the flow rate through the vein 410, the net flow volume through the portion of the subject's body, a current position of the chest compressions, an identity or position of the artery 408 in the subject's body, an identity or position of the vein 410 in the subject's body, or any combination thereof. For example, if the chest compressions are being administered to the right of an ideal position, the flow monitor 402 may detect a peak and/or mean flow rate of blood in the artery 408 that is below a threshold. In various implementations, the flow monitor 402 (or another computing device that is communicatively coupled to the flow monitor 402) generates a feedback signal including an instruction to apply the chest compressions one direction or another and/or closer to the ideal position.

According to various implementations, the flow monitor 402 can detect the presence of spontaneous circulation of the subject, in which the heart of the subject is spontaneously pumping a sufficient amount of blood through the body of the subject. In some cases, the flow monitor 402 detects a return of spontaneous circulation (ROSC). The flow monitor 402, for instance, can detect spontaneous circulation while the subject is receiving chest compressions. As noted previously, when the subject is receiving chest compressions, the chest compressions cause parallel or unidirectional blood flow in the artery 408 and the vein 410. In contrast, the pumping heart of the subject circulating blood through the subject's circulatory system causes antiparallel or bidirectional blood flow in the artery 408 and the vein 410. Thus, the flow monitor 402, in some cases, detects spontaneous circulation in response to detecting antiparallel or bidirectional blood flow in the artery 408 and vein 410.

In some cases, the flow monitor 402 detects spontaneous circulation using other techniques. In general, the heart is capable of pumping blood at a greater peak velocity than chest compressions. Therefore, the monitor 402 may detect spontaneous circulation by detecting that a blood velocity through the artery 408 or the vein 410 is greater than a threshold. Further, the blood velocity through the artery 408 or the vein 410 with respect to time during chest compressions is different than the blood velocity through the artery 408 or the vein 410 with respect to time during spontaneous circulation. According to some implementations, the flow monitor detects spontaneous circulation by determining that at least one frequency component of the volumetric flow rate over time through the artery 408 or vein 410 has changed.

For instance, a shape or morphology of the volumetric flow rate over time can be indicative of spontaneous circulation.

Certain functionalities of the flow monitor 402 are enhanced by communications with other devices, such as the mechanical chest compression device 426 and a monitor-defibrillator 428. Collectively, any combination of the flow monitor 402, the mechanical chest compression device 426, and the monitor-defibrillator 428 may be a resuscitation system that is configured to resuscitate a single subject. For example, the flow monitor 402 is configured to modify and/or temporally gate measurements it performs based on communications from the mechanical chest compression device 426 and/or the monitor-defibrillator 428. In some cases, the flow monitor 402 receives a communication signal from the mechanical chest compression device 426 that indicates a frequency of chest compressions administered by the mechanical chest compression device 426, a timing of chest compressions administered by the mechanical chest compression device 426, or a time of a pause in the chest compressions administered by the mechanical chest compression device 426. In some cases, the flow monitor 402 is configured to remove a chest compression artifact from a blood velocity over time based on the communication signal from the mechanical chest compression device 426. For instance, the flow monitor 402 may remove an artifact from the blood velocity by applying a band reject filter centered around the chest compression frequency or by applying a comb filter that includes the chest compression frequency and one or more harmonics of the chest compression frequency. In some cases, the flow monitor 402 is configured to temporally gate a blood velocity measurement during a time window in which the mechanical chest compression device 426 has paused chest compressions or between chest compressions performed by the chest compression device 426. Using these techniques, in some cases, may enable the flow monitor 402 to more accurately identify spontaneous circulation of the subject by distinguishing between blood flow caused by the chest compressions and spontaneous blood flow induced by the heart of the subject.

In some cases, the monitor-defibrillator 428 transmits a communication signal to the flow monitor 402 indicating a time at which the monitor-defibrillator 428 is administering a treatment to the subject, such as an electrical shock or pace pulses. Because the electrical shock or pace pulses can interfere with the accuracy of other measurements performed by the flow monitor 402, the flow monitor 402 may gate the measurements at a time interval that omits the treatment to the subject. In some implementations, the flow monitor 402 includes sensitive electronics that could potentially be damaged when the treatment is administered to the subject. According to some examples, the flow monitor 402 includes a circuit with at least one switch that disconnects or otherwise shields the sensitive electronics during the treatment.

In some examples, the flow monitor 402 includes or is otherwise communicatively coupled to devices that include one or more sensors (not illustrated) configured to detect other physiological parameters. For example, the flow monitor 402 includes or is communicatively coupled with a sensor configured to detect an electrocardiogram (ECG), an oximetry sensor (e.g., a regional oximetry sensor, a pulse oximetry sensor, a cerebral oximetry sensor, or the like), or both.

In various implementations, the flow monitor 402 includes one or more accelerometers 430 configured to detect an acceleration of the flow monitor 402 and/or the skin 404 of the subject. The acceleration, for instance, is indicative of chest compressions administered to the subject or a pulse of the subject through the artery 408 or vein 410. Thus, in some cases, the flow monitor 402 detects whether the subject has a pulse based on the acceleration detected by the accelerometer(s) 430. At least one additional accelerometer 432 may further be disposed on another portion of the subject (e.g., the subject's chest) and may be configured to detect an acceleration indicative of the chest compressions. The flow monitor 402, in some implementations, removes a chest compression artifact of the acceleration detected by the accelerometer(s) 430 over time based on the acceleration detected by the additional accelerometer(s) 432 over time. In various implementations, the flow monitor 402 is configured to accurately detect spontaneous circulation or another condition of the subject based on the detected accelerations.

As used herein, the term "measurement" may refer to a blood velocity, a net blood flow volume, an ECG, an oxygenation of the subject's blood, an acceleration, or another physiological parameter of the subject. In some cases, the flow monitor 402 validates and/or temporally gates a first measurement in view of a second measurement. For example, if the ECG indicates that the heart of the subject is beating, but the blood velocity or net blood flow indicates that oxygenated blood is not circulating in the subject, then the flow monitor 402 may refrain from indicating that the subject has spontaneous circulation. In some cases, the flow monitor 402 may output a signal indicating that the subject has pulseless electrical activity (PEA).

In various cases, the flow monitor 402 is configured to detect blood flow in the brain of the subject. In some cases, the artery 408 is a part of the circle of Willis of the subject. If the subject is an adult, the skull of the subject may highly attenuate the first incident beam 414, the second incident beam 416, the first return beam 418, and the second return beam 420. For instance, the skull may have high attenuation with respect to ultrasound and/or light (e.g., at certain frequencies). Thus, in various examples, the flow monitor 402 is configured to direct the first incident beam 414, the second incident beam 416, the first return beam 418, and the second return beam 420 through a window in the skull. For instance, the flow monitor 402 is configured to monitor the artery 408 and/or vein 410 through a temple of the subject, an orbital socket of the subject, or an ear canal of the subject. In some cases, the flow monitor 402 is strapped to the head of the subject, such as in the form of an eyepatch.

In some cases, the operation of the flow monitor 402 is optimized in other ways to enable monitoring within the brain. For instance, if the first incident beam 414 and the second incident beam 416 include ultrasound, the ultrasound may have a frequency of less than 1 MHZ. Although sub MHz ultrasound is incapable of generating high-resolution images, in some cases, the flow monitor 402 detects the flow through the artery 408 or vein 410 without generating an image of the artery 408 or vein 410. That is, sub MHz ultrasound is sufficient for Doppler flow detection in various implementations described herein.

Another way in which the flow monitor 402 is optimized for monitoring with the brain relates to the type of the artery 408 and/or vein 410 monitored by the flow monitor 402. Attenuation of an incident beam increases as it travels through an attenuating structure. Thus, in some cases, a distance between the flow monitor 402 (e.g., disposed on the skin 404 or eye) is less than a threshold distance.

In particular cases, it may be difficult to differentiate specific blood vessels in the brain (e.g., within the Circle of Willis) in which the first return beam 418 and/or the second return beam 420 are reflected and/or scattered. Further, it may be difficult to identify angles from which the blood vessels in the brain are disposed with respect to the flow monitor 402. Accordingly, it may be difficult to accurately quantify blood flow parameters of a blood vessel in the brain using techniques described herein. However, even detecting the presence or absence of movement of blood in the brain can provide helpful feedback in order to detect chest compression efficacy and/or spontaneous circulation. According to various implementations, the flow monitor 402 outputs an indication if the flow monitor 402 detects movement, or the absence of movement, or the relative difference of movement between the compression and decompression parts of CPR or the diastolic and systolic parts of a normal sinus rhythm of blood in the brain of the subject.

By detecting blood flow in the brain, the flow monitor 402 is configured to detect an efficacy of chest compressions being administered to the subject. Technologies that monitor blood flow in extremities can indirectly detect chest compression efficacy. However, because a primary purpose of chest compressions is to provide oxygenated blood to the brain of the subject, the flow monitor 402 is able to directly detect the efficacy of the chest compressions by monitoring blood flow in the brain. The flow monitor 402, for instance, can output a feedback signal (e.g., to the mechanical chest compression device 426 or to the user) indicating whether chest compressions are generating blood flow in the brain. In some cases, the feedback signal includes a metric indicative of the blood flow in the brain (e.g., a quantity that increases with an increase in a detected blood velocity or flow rate).

According to some examples, the receiver(s) 422 include one or more microphones configured to detect an audible sound 434 from the subject. For example, the flow monitor 402 may include the functionality of a sophisticated stethoscope. In some cases, the microphone(s) detect the audible sound 434 emitted by blood flowing through the artery 408 or vein 410. In some examples, the microphone(s) detect the audible sound 434 emitted by the heart of the subject. In various implementations, the audible sound 434 can be in an audible or inaudible range. The flow monitor 402, in various cases, detects the audible sound 434 at a sampling frequency, such as a sampling frequency of greater than 400 Hz, 4 kHz, or 40 kHz. In some implementations, the flow monitor 402 determines a condition of the subject based on the audible sound 434.

According to some cases, the output device(s) 424 include a speaker that outputs an audible signal indicative of the audible sound 434 detected by the flow monitor 402. For example, the output device(s) 424 output the sampled audible sound 434 into an audio headset of the user, or in an environment in which the user is present, at a volume that can be perceived by the user in an emergency scene. That is, the output device(s) 424 may amplify the audible sound 434. Some monitors output computer-generated sounds indicative of a heart rate of a subject, such as a "beep" sound whenever a QRS complex is detected in an ECG. According to some implementations, the audible sound 434 includes more diagnostic-relevant information that can be perceived by the user than a computerized "beep" sound. In some examples, a condition of the subject can be identified using the strength, velocity, or morphological characteristics of blood flow, but these features cannot necessarily be identified using audio output from a previous type of monitor. Furthermore, by outputting an amplified version of the audible sound 434 as an audible signal, the flow monitor 402 may convey potentially important information about the condition of the subject without visually outputting it on a display. The user, for example, may be monitoring other visual signals on the monitor-defibrillator 428, and thus the flow monitor 402 may enable cognitive offloading for the user.

In some implementations, the receiver(s) 422 include multiple microphones configured to detect audible sounds 434 from multiple locations on the subject's body. For instance, the microphones may detect the audible sound 434 from a right quadrant of the subject's chest and another audible sound 434 from a left quadrant of the subject's chest. The flow monitor 402, in some cases, analyzes the detected sounds for features indicative of a medical condition. For example, the flow monitor 402 detects the medical condition by detecting an anomaly in the detected sound. In some implementations, the flow monitor 402 selectively outputs a single one of the audible sounds based on an input signal received from the user. In some cases, the flow monitor 402 selectively outputs a single one of the audible sounds that is indicative of the medical condition. In various implementations, the output device(s) 424 are configured to output a signal indicating the medical condition.

Figure 5:
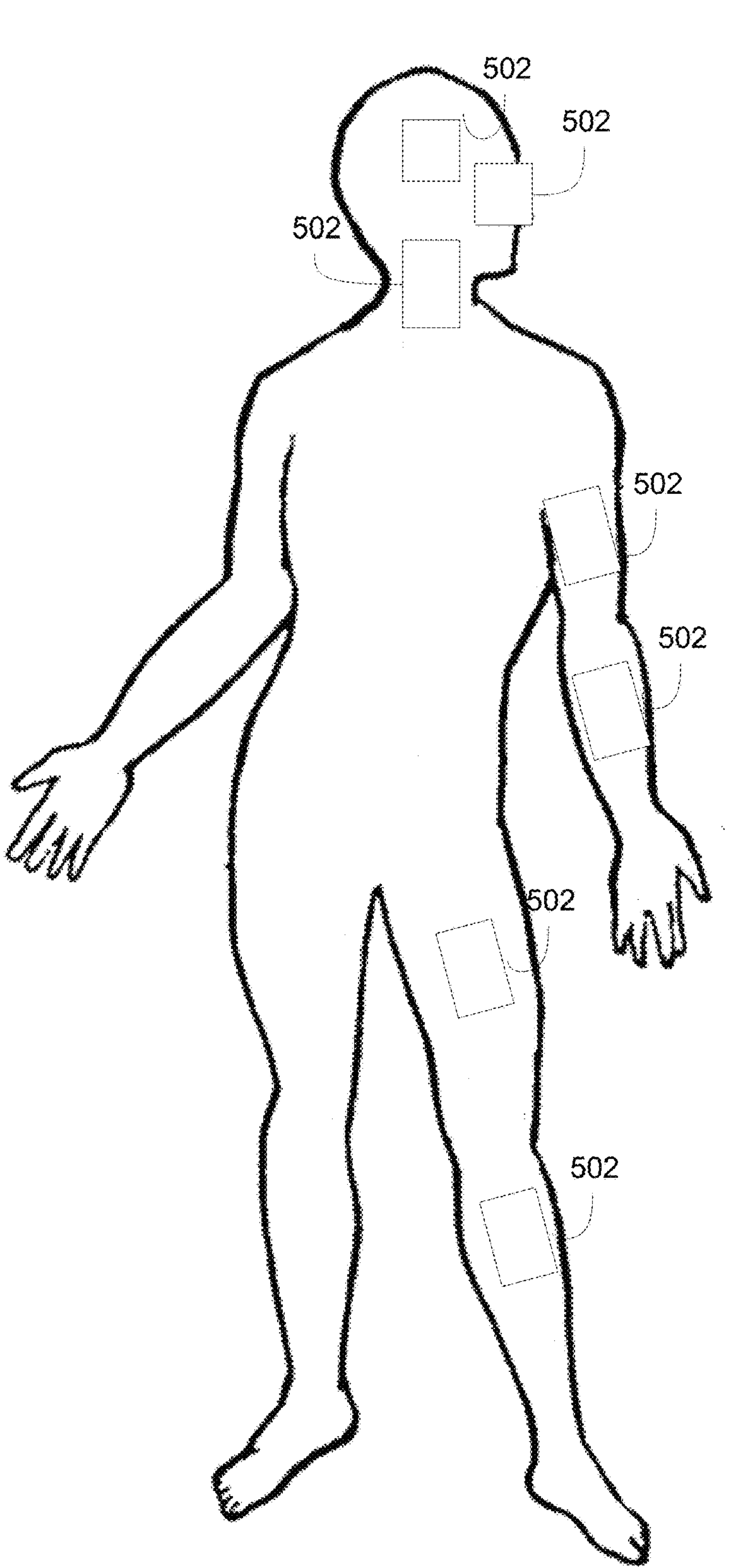
FIG. 5 illustrates various placements of the flow monitor on the body of a subject.

FIG. 5 illustrates various placements of the flow monitor 502 on the body of a subject 500. For example, the flow monitor 502 may be disposed on a temple, an orbital socket, an ear canal, a neck, an upper arm, a lower arm, an upper leg, or a lower leg of the subject 500. In some implementations, the flow monitor 502 includes multiple physical devices that are disposed on different parts of the body of the subject 500, simultaneously. In various implementations, the flow monitor 502 may be integrated into a cot or other support on which the subject 500 is disposed.

Figure 6:
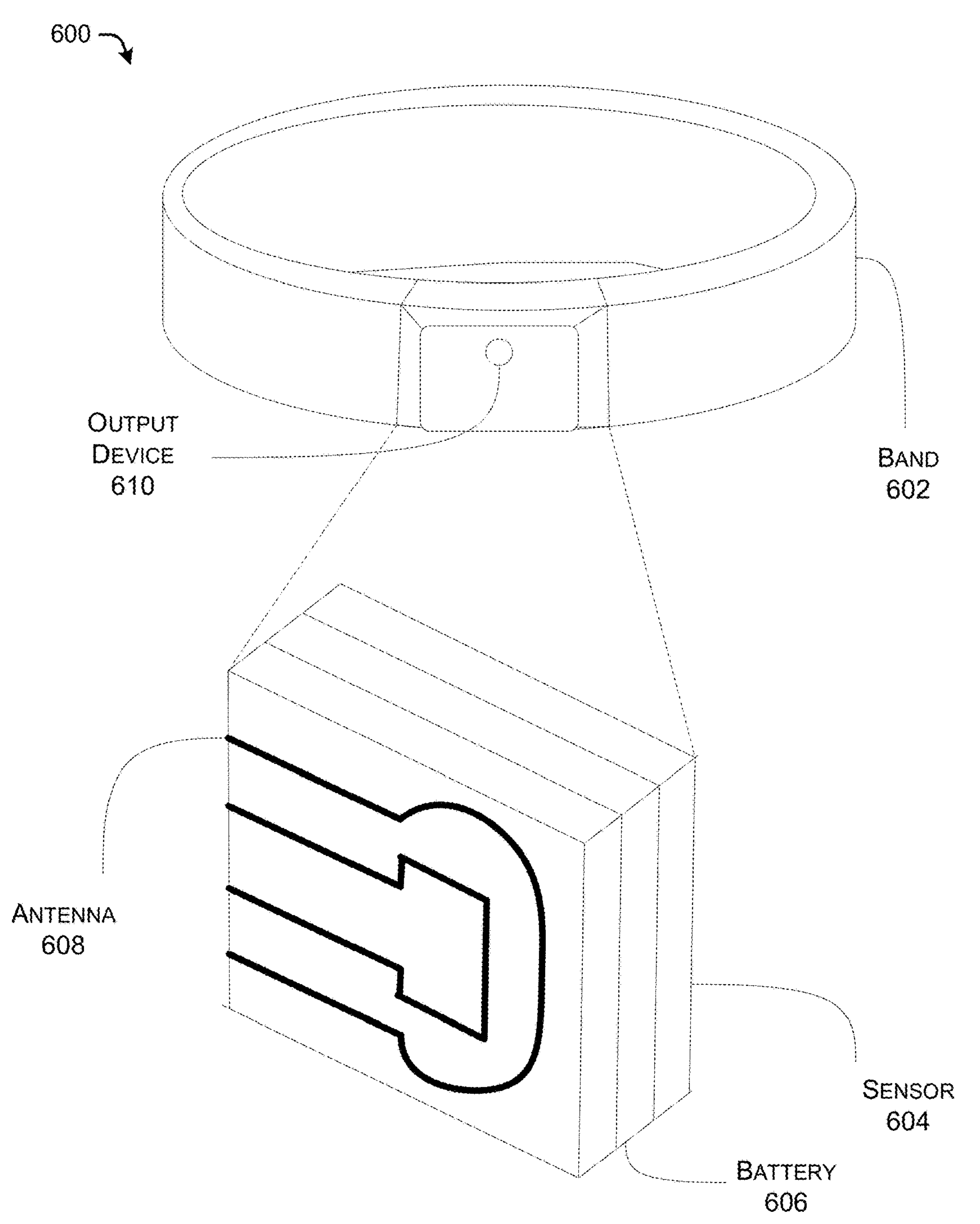
FIG. 6 illustrates the structure of an example flow monitor.

FIG. 6 illustrates the structure of an example flow monitor 600. In some cases, the flow monitor 600 is a patch that can be strapped to a subject or adhered to the skin of the subject. For instance, the flow monitor 600 includes a band 602 configured to be disposed around an appendage of the subject. According to some examples, the band 602 is configured to be disposed around a chest, abdomen, head, or neck of the subject.

In various implementations, the flow monitor 600 includes a sensor 604 configured to detect a physiological parameter indicative of blood flow through a subject. In some cases, the sensor 604 includes a microphone configured to detect a sound generated by the body of the subject. In some examples, the sensor 604 includes an ultrasound transducer configured to detect the velocity of blood flowing through at least one blood vessel of the subject and/or through the heart of the subject. In some examples, the sensor 604 includes an ultrasound transducer configured to detect heart wall motion. In some cases, the sensor 604 includes at least one transmitter and/or at least one receiver. In some examples, the sensor 604 includes one or more accelerometers.

The sensor 604, for instance, is powered by a battery 606. In some cases, the battery 606 is disposable. In some examples, the battery 606 is rechargeable.

The flow monitor 600, in various cases, further includes an antenna 608. The antenna 608, in various implementations, is configured to transmit and/or receive communication signals from an external device. In some cases, the antenna 608 enables the flow monitor 600 to communicate with another flow monitor or another type of medical device (e.g., an AED or monitor-defibrillator). For instance, the flow monitor 600 is configured to transmit, to an external device, an indication of the physiological parameter detected by the sensor 604. The antenna 608, in various cases, is powered by the battery 606.

According to various examples, the sensor 604, the battery 606, and the antenna 608 are arranged in respective layers of the flow monitor 600. For example, each layer may correspond to a circuit board (e.g., a PCB) that accommodates a respective component. In various cases, the layer corresponding to the sensor 604 is configured to be adjacent to the subject when the flow monitor 600 is disposed on the subject. The layer corresponding to the antenna 608, for example, faces away from the subject when the flow monitor 600 is disposed on the subject. Accordingly, the body of the subject may be prevented from interfering with wireless signals transmitted and/or received by the antenna 608.

In some examples, the flow monitor 600 further includes an output device 610. The output device 610 is configured to output a signal to a user. In some cases, the signal is based on the physiological parameter detected by the sensor 604. For instance, the output device 610 includes a light that is activated when a blood velocity detected by the sensor 604 remains below a threshold blood velocity for greater than a threshold period of time.

Figure 7:
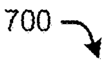
FIG. 7 illustrates an example process for detecting whether blood is spontaneously flowing through the body of a subject.
Figure 7:
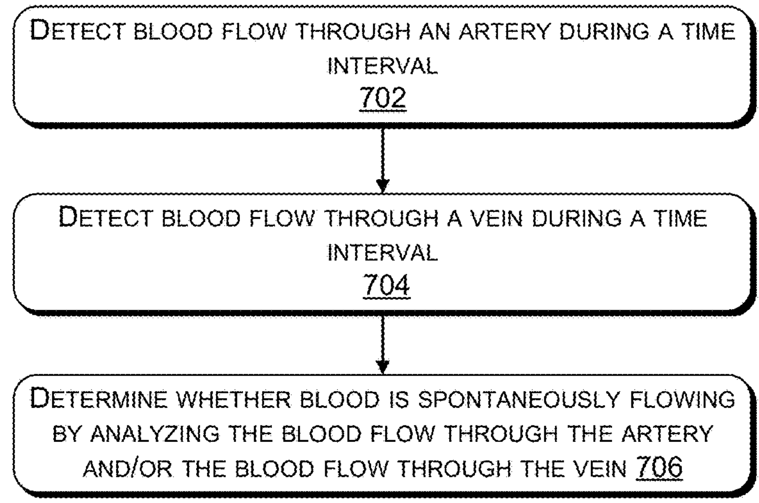
Figure 8:
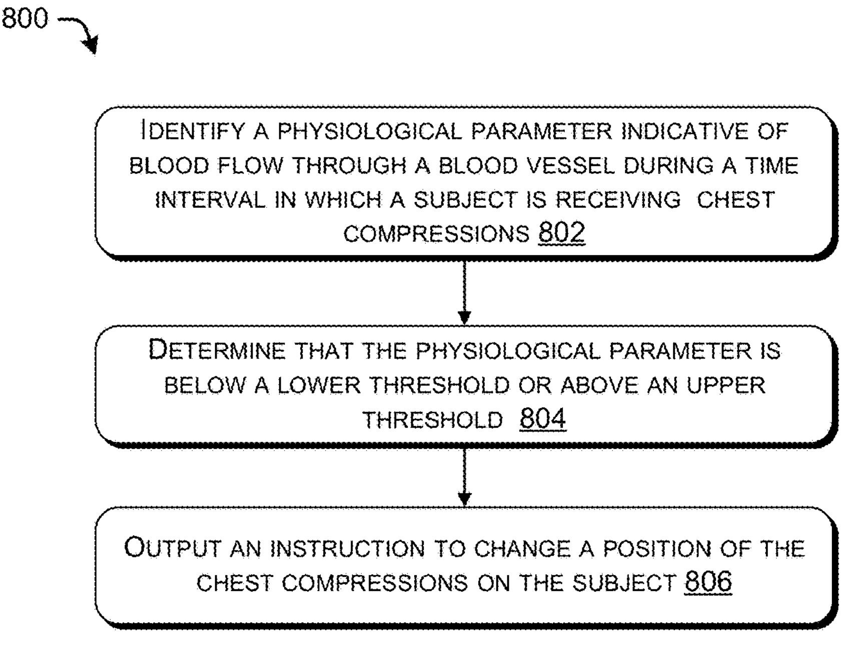
FIG. 8 illustrates an example process for optimizing chest compressions administered to a subject.

FIGS. 7 and 8 illustrate various processes related to implementations of the present disclosure. Although steps in the processes are illustrated as being performed in a particular order, implementations are not necessarily limited to the orders illustrated. Further, in some cases, the processes may be performed multiple times (e.g., periodically).

FIG. 7 illustrates an example process 700 for detecting whether blood is spontaneously flowing through the body of a subject. The process 700 is performed by an entity including, for example, a flow monitor (e.g., the flow monitor 106, flow monitor 402, flow monitor 502, or any combination thereof), a medical device, a monitor-defibrillator (e.g., the monitor-defibrillator 428), a mechanical chest compression device (e.g., the mechanical chest compression device 104 and/or the mechanical chest compression device 426), at least one computing device (e.g., the output device 122), at least one processor, or any combination thereof.

At 702, the entity detects blood flow through an artery during a time interval. For instance, the entity determines a Doppler shift of an incident beam (e.g., an ultrasound beam) that is reflected from blood flowing through the artery.

At 704, the entity detects blood flow through a vein during the time interval. For instance, the entity determines a Doppler shift of an incident beam (e.g., an ultrasound beam) that is reflected from blood flowing through the vein. In some cases, the blood flow through the vein is determined based on a reflection of the same incident beam used to determine the Doppler shift of the blood flow through the artery. In some examples, a different incident beam is used to detect the blood flow through the vein. In various implementations, the vein is paired with the artery. For example, during spontaneous circulation and respiration, oxygenated blood flows through the artery into a physiological structure of a subject and deoxygenated blood flow through the vein from the physiological structure of the subject. The artery and the vein, in various cases, are substantially parallel to each other in the body of the subject. For instance, the artery may be a carotid artery and the vein may be a jugular vein.

At 706, the entity determines whether blood is spontaneously flowing by analyzing the blood flow through the artery and/or the blood flow through the vein. In some cases, the blood flow through the artery during a time interval is compared to the blood flow through the vein during the same time interval. For example, the directions of blood flow through the artery and the vein are compared. In some cases, the entity determines that the subject has received one or more chest compressions during the time interval if the blood flow through the artery is parallel to the blood flow through the vein (e.g., the blood flow in the artery and vein is traveling toward a heart of the subject or away from the heart of the subject). If, however, the directions are antiparallel (e.g., the blood flow in the artery is moving away from the heart and the blood flow in the vein is moving toward the heart), then the entity may infer that blood is spontaneously circulating.

In some examples, the entity determines that the subject has received one or more chest compressions during the time interval if the blood flow through the vein is indicative of pulsatile flow. However, if the entity determines that the blood flow through the vein is non-pulsatile, then the entity may infer that blood is spontaneously circulating in the body of the subject.

According to some instances, the entity determines that the subject has received one or more chest compressions during the time interval if a ratio of the amplitude of blood flow through the artery and the amplitude of blood flow through the vein is below a threshold. This ratio, for instance, compares pulsatility in the artery to pulsatility in the vein. In various cases, the entity determines that blood is spontaneously circulating in the body of the subject if the ratio is above or equal to the threshold. That is, the entity may infer that blood is spontaneously circulating if the amplitude of blood flow through the artery is significantly greater than the amplitude of blood flow through the vein.

According to some cases, the entity uses the blood flow through the artery and vein to provide chest compression feedback. For example, the entity may determine a velocity or volume of blood flowing through the artery and a velocity or volume of blood flowing through the vein, during the same time interval. The entity may determine whether one or more chest compressions being administered to the subject are effective based on the velocities or volumes of blood. For example, the entity may determine that the chest compression(s) is effective by determining that an amplitude of the velocity or volume of blood flowing through the vein is above a first threshold and/or that an amplitude of the velocity or volume of blood flowing through the artery is above a second threshold.

In various implementations, the entity further outputs an indication of whether the blood is spontaneously circulating through the body of the subject. For example, the entity may output a visual or audible signal that indicates, to a user, that blood is spontaneously circulating. In some cases, the entity outputs an instruction to cease administering chest compressions in response to determining that blood is spontaneously circulating.

FIG. 8 illustrates an example process 800 for optimizing chest compressions administered to a subject. The process 800 is performed by an entity including, for example, a flow monitor (e.g., the flow monitor 106, flow monitor 402, flow monitor 502, or any combination thereof), a medical device, a monitor-defibrillator (e.g., the monitor-defibrillator 428), a mechanical chest compression device (e.g., the mechanical chest compression device 104 and/or the mechanical chest compression device 426), at least one computing device (e.g., the output device 122), at least one processor, or any combination thereof.

At 802, the entity identifies a physiological parameter indicative of blood flow through a blood vessel during a time interval in which the subject is receiving chest compressions. For instance, the physiological parameter is a velocity of blood flow or a volume of blood flow through one or more cross-sections of the blood vessel during the time interval. In some examples, the entity identifies the physiological parameter based on a Doppler shift between an incident beam transmitted toward the blood in the blood vessel and a reflection of the incident beam from the blood in the blood vessel. In various implementations, the blood vessel is an artery.

At 804, the entity determines that the physiological parameter is below a lower threshold or above an upper threshold. In some implementations, the physiological parameter being below the lower threshold indicates that the blood flow is insufficient to adequately oxygenate one or more portions of the subject. In some cases, the physiological parameter being above the upper threshold indicates that the blood flow is so substantial that it could damage one or more portions of the subject (e.g., vasculature of the subject).

At 806, the entity outputs an instruction to change a position of the chest compressions on the subject. For instance, if the blood flow is determined to be insufficient, the entity may output an instruction to move the position of the chest compressions toward the heart of the subject (e.g., toward the center of the subject's chest). In contrast, if the blood flow is determined to be excessive, the entity may output an instruction to move the position of the chest compressions away from the heart of the subject (e.g., away from the center of the subject's chest). The chest compressions, for instance, may be administered by a mechanical chest compression device. In some of these cases, the instruction may be in a communication signal transmitted to the mechanical chest compression device. In some examples, the chest compressions are manually administered by a rescuer. For example, the instruction may be output to the user visually via a display, audibly via a speaker, or the like. In some cases, the instruction further directs a change in one or more additional chest compression parameters, such as a duty cycle, speed, height of recoil, depth, or frequency of the chest compressions.

Figure 9:
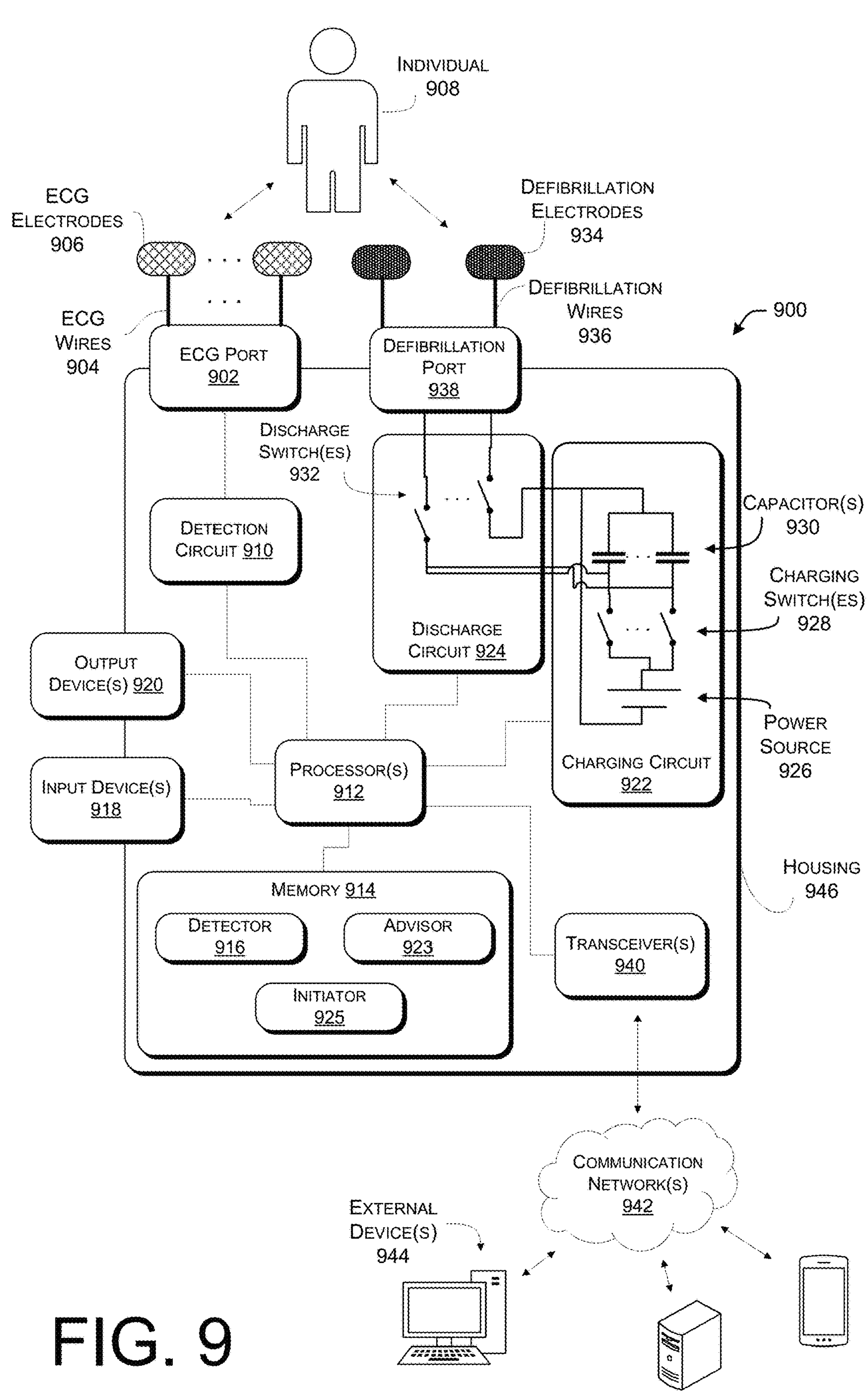
FIG. 9 illustrates an example of an external defibrillator configured to perform various functions described herein.

FIG. 9 illustrates an example of an external defibrillator 900 configured to perform various functions described herein. For example, the external defibrillator 900 is the monitor-defibrillator 428 described above with reference to FIG. 4.

The external defibrillator 900 includes an electrocardiogram (ECG) port 902 connected to multiple ECG wires 904. In some cases, the ECG wires 904 are removeable from the ECG port 902. For instance, the ECG wires 904 are plugged into the ECG port 902. The ECG wires 904 are connected to ECG electrodes 906, respectively. In various implementations, the ECG electrodes 906 are disposed on different locations on an individual 908. A detection circuit 910 is configured to detect relative voltages between the ECG electrodes 906. These voltages are indicative of the electrical activity of the heart of the individual 908.

In various implementations, the ECG electrodes 906 are in contact with the different locations on the skin of the individual 908. In some examples, a first one of the ECG electrodes 906 is placed on the skin between the heart and right arm of the individual 908, a second one of the ECG electrodes 906 is placed on the skin between the heart and left arm of the individual 908, and a third one of the ECG electrodes 906 is placed on the skin between the heart and a leg (either the left leg or the right leg) of the individual 908. In these examples, the detection circuit 910 is configured to measure the relative voltages between the first, second, and third ECG electrodes 906. Respective pairings of the ECG electrodes 906 are referred to as "leads," and the voltages between the pairs of ECG electrodes 906 are known as "lead voltages." In some examples, more than three ECG electrodes 906 are included, such that 5-lead or 12-lead ECG signals are detected by the detection circuit 910.

The detection circuit 910 includes at least one analog circuit, at least one digital circuit, or a combination thereof. The detection circuit 910 receives the analog electrical signals from the ECG electrodes 906, via the ECG port 902 and the ECG wires 904. In some cases, the detection circuit 910 includes one or more analog filters configured to filter noise and/or artifact from the electrical signals. The detection circuit 910 includes an analog-to-digital converter (ADC) in various examples. The detection circuit 910 generates a digital signal indicative of the analog electrical signals from the ECG electrodes 906. This digital signal can be referred to as an "ECG signal" or an "ECG."

In some cases, the detection circuit 910 further detects an electrical impedance between at least one pair of the ECG electrodes 906. For example, the detection circuit 910 includes, or otherwise controls, a power source that applies a known voltage (or current) across a pair of the ECG electrodes 906 and detects a resultant current (or voltage) between the pair of the ECG electrodes 906. The impedance is generated based on the applied signal (voltage or current) and the resultant signal (current or voltage). In various cases, the impedance corresponds to respiration of the individual 908, chest compressions performed on the individual 908, and other physiological states of the individual 908. In various examples, the detection circuit 910 includes one or more analog filters configured to filter noise and/or artifact from the resultant signal. The detection circuit 910 generates a digital signal indicative of the impedance using an ADC. This digital signal can be referred to as an "impedance signal" or an "impedance."

The detection circuit 910 provides the ECG signal and/or the impedance signal one or more processors 912 in the external defibrillator 900. In some implementations, the processor(s) 912 includes a central processing unit (CPU), a graphics processing unit (GPU), digital signal processing unit (DPU), other processing unit or component known in the art, or any combination thereof.

The processor(s) 912 is operably connected to memory 914. In various implementations, the memory 912 is volatile (such as random access memory (RAM)), non-volatile (such as read only memory (ROM), flash memory, etc.) or some combination of the two. The memory 914 stores instructions that, when executed by the processor(s) 912, causes the processor(s) 912 to perform various operations. In various examples, the memory 914 stores methods, threads, processes, applications, objects, modules, any other sort of executable instruction, or a combination thereof. In some cases, the memory 914 stores files, databases, or a combination thereof. In some examples, the memory 914 includes, but is not limited to, RAM, ROM, electrically erasable programmable read-only memory (EEPROM), flash memory, or any other memory technology. In some examples, the memory 914 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 912 and/or the external defibrillator 900. In some cases, the memory 914 at least temporarily stores the ECG signal and/or the impedance signal.

In various examples, the memory 914 includes a detector 916, which causes the processor(s) 912 to determine, based on the ECG signal and/or the impedance signal, whether the individual 908 is exhibiting a particular heart rhythm. For instance, the processor(s) 912 determines whether the individual 908 is experiencing a shockable rhythm that is treatable by defibrillation. Examples of shockable rhythms include ventricular fibrillation (VF) and ventricular tachycardia (VT). In some examples, the processor(s) 912 determines whether any of a variety of different rhythms (e.g., asystole, sinus rhythm, atrial fibrillation (AF), etc.) are present in the ECG signal.

The processor(s) 912 is operably connected to one or more input devices 918 and one or more output devices 920. Collectively, the input device(s) 918 and the output device(s) 920 function as an interface between a user and the defibrillator 900. The input device(s) 918 is configured to receive an input from a user and includes at least one of a switch, a keypad, a cursor control, a touch-sensitive display, a voice input device (e.g., a microphone), a haptic feedback device (e.g., a gyroscope), or any combination thereof. The output device(s) 920 includes at least one of a display, a speaker, a haptic output device, a printer, a light indicator such as an LED, or any combination thereof. In various examples, the processor(s) 912 causes a display among the input device(s) 918 to visually output a waveform of the ECG signal and/or the impedance signal. In some implementations, the input device(s) 918 includes one or more touch sensors, the output device(s) 920 includes a display screen, and the touch sensor(s) are integrated with the display screen. Thus, in some cases, the external defibrillator 900 includes a touchscreen configured to receive user input signal(s) and visually output physiological parameters, such as the ECG signal and/or the impedance signal.

In some examples, the memory 914 includes an advisor 923, which, when executed by the processor(s) 912, causes the processor(s) 912 to generate advice and/or control the output device(s) 920 to output the advice to a user (e.g., a rescuer). In some examples, the processor(s) 912 provides, or causes the output device(s) 920 to provide, an instruction to perform CPR on the individual 908. In some cases, the processor(s) 912 evaluates, based on the ECG signal, the impedance signal, or other physiological parameters, CPR being performed on the individual 908 and causes the output device(s) 920 to provide feedback about the CPR in the instruction. According to some examples, the processor(s) 912, upon identifying that a shockable rhythm is present in the ECG signal, causes the output device(s) 920 to output an instruction and/or recommendation to administer a defibrillation shock to the individual 908.

The memory 914 also includes an initiator 925 which, when executed by the processor(s) 912, causes the processor(s) 912 to control other elements of the external defibrillator 900 in order to administer a defibrillation shock to the individual 908. In some examples, the processor(s) 912 executing the discharge circuit 924 selectively causes the administration of the defibrillation shock based on determining that the individual 908 is exhibiting the shockable rhythm and/or based on an input from a user (received, e.g., by the input device(s) 918. In some cases, the processor(s) 912 causes the defibrillation shock to be output at a particular time, which is determined by the processor(s) 912 based on the ECG signal and/or the impedance signal.

The processor(s) 912 is operably connected to a charging circuit 922 and a discharge circuit 924. In various implementations, the charging circuit 922 includes a power source 926, one or more charging switches 928, and one or more capacitors 930. The power source 926 includes, for instance, a battery. The processor(s) 912 initiates a defibrillation shock by causing the power source 926 to charge at least one capacitor among the capacitor(s) 930. For example, the processor(s) 912 activates at least one of the charging switch(es) 928 in the charging circuit 922 to complete a first circuit connecting the power source 926 and the capacitor to be charged. Then, the processor(s) 912 causes the discharge circuit 924 to discharge energy stored in the charged capacitor across a pair of defibrillation electrodes 934, which are in contact with the individual 908. For example, the processor(s) 912 deactivates the charging switch(es) 928 completing the first circuit between the capacitor(s) 930 and the power source 926, and activates one or more discharge switches 932 completing a second circuit connecting the charged capacitor 930 and at least a portion of the individual 908 disposed between defibrillation electrodes 934.

The energy is discharged from the defibrillation electrodes 934 in the form of a defibrillation shock. For example, the defibrillation electrodes 934 are connected to the skin of the individual 908 and located at positions on different sides of the heart of the individual 908, such that the defibrillation shock is applied across the heart of the individual 908. The defibrillation shock, in various examples, depolarizes a significant number of heart cells in a short amount of time. The defibrillation shock, for example, interrupts the propagation of the shockable rhythm (e.g., VF or VT) through the heart. In some examples, the defibrillation shock is 200 J or greater with a duration of about 0.015 seconds. In some cases, the defibrillation shock has a multiphasic (e.g., biphasic) waveform. The discharge switch(es) 932 are controlled by the processor(s) 912, for example. In various implementations, the defibrillation electrodes 934 are connected to defibrillation wires 936. The defibrillation wires 936 are connected to a defibrillation port 938, in implementations. According to various examples, the defibrillation wires 936 are removable from the defibrillation port 938. For example, the defibrillation wires 936 are plugged into the defibrillation port 938.

In various implementations, the processor(s) 912 is operably connected to one or more transceivers 940 that transmit and/or receive data over one or more communication networks 942. For example, the transceiver(s) 940 includes a network interface card (NIC), a network adapter, a local area network (LAN) adapter, or a physical, virtual, or logical address to connect to the various external devices and/or systems. In various examples, the transceiver(s) 940 includes any sort of wireless transceivers capable of engaging in wireless communication (e.g., radio frequency (RF) communication). For example, the communication network(s) 942 includes one or more wireless networks that include a 3$^{rd}$ Generation Partnership Project (3GPP) network, such as a Long Term Evolution (LTE) radio access network (RAN) (e.g., over one or more LTE bands), a New Radio (NR) RAN (e.g., over one or more NR bands), or a combination thereof. In some cases, the transceiver(s) 940 includes other wireless modems, such as a modem for engaging in WI-FI®, WIGIG®, WIMAX®, BLUETOOTH®, or infrared communication over the communication network(s) 942.

The defibrillator 900 is configured to transmit and/or receive data (e.g., ECG data, impedance data, data indicative of one or more detected heart rhythms of the individual 908, data indicative of one or more defibrillation shocks administered to the individual 908, etc.) with one or more external devices 944 via the communication network(s) 942. The external devices 944 include, for instance, mobile devices (e.g., mobile phones, smart watches, etc.), Internet of Things (IoT) devices, medical devices (e.g., a flow monitor), computers (e.g., laptop devices, servers, etc.), or any other type of computing device configured to communicate over the communication network(s) 942. In some examples, the external device(s) 944 is located remotely from the defibrillator 900, such as at a remote clinical environment (e.g., a hospital). According to various implementations, the processor(s) 912 causes the transceiver(s) 940 to transmit data to the external device(s) 944. In some cases, the transceiver(s) 940 receives data from the external device(s) 944 and the transceiver(s) 940 provide the received data to the processor(s) 912 for further analysis.

In various implementations, the external defibrillator 900 also includes a housing 946 that at least partially encloses other elements of the external defibrillator 900. For example, the housing 946 encloses the detection circuit 910, the processor(s) 912, the memory 914, the charging circuit 922, the transceiver(s) 940, or any combination thereof. In some cases, the input device(s) 918 and output device(s) 920 extend from an interior space at least partially surrounded by the housing 946 through a wall of the housing 946. In various examples, the housing 946 acts as a barrier to moisture, electrical interference, and/or dust, thereby protecting various components in the external defibrillator 900 from damage.

In some implementations, the external defibrillator 900 is an automated external defibrillator (AED) operated by an untrained user (e.g., a bystander, layperson, etc.) and can be operated in an automatic mode. In automatic mode, the processor(s) 912 automatically identifies a rhythm in the ECG signal, makes a decision whether to administer a defibrillation shock, charges the capacitor(s) 930, discharges the capacitor(s) 930, or any combination thereof. In some cases, the processor(s) 912 controls the output device(s) 920 to output (e.g., display) a simplified user interface to the untrained user. For example, the processor(s) 912 refrains from causing the output device(s) 920 to display a waveform of the ECG signal and/or the impedance signal to the untrained user, in order to simplify operation of the external defibrillator 900.

In some examples, the external defibrillator 900 is a monitor-defibrillator utilized by a trained user (e.g., a clinician, an emergency responder, etc.) and can be operated in a manual mode or the automatic mode. When the external defibrillator 900 operates in manual mode, the processor(s) 912 cause the output device(s) 920 to display a variety of information that may be relevant to the trained user, such as waveforms indicating the ECG data and/or impedance data, notifications about detected heart rhythms, and the like.

Figure 10:
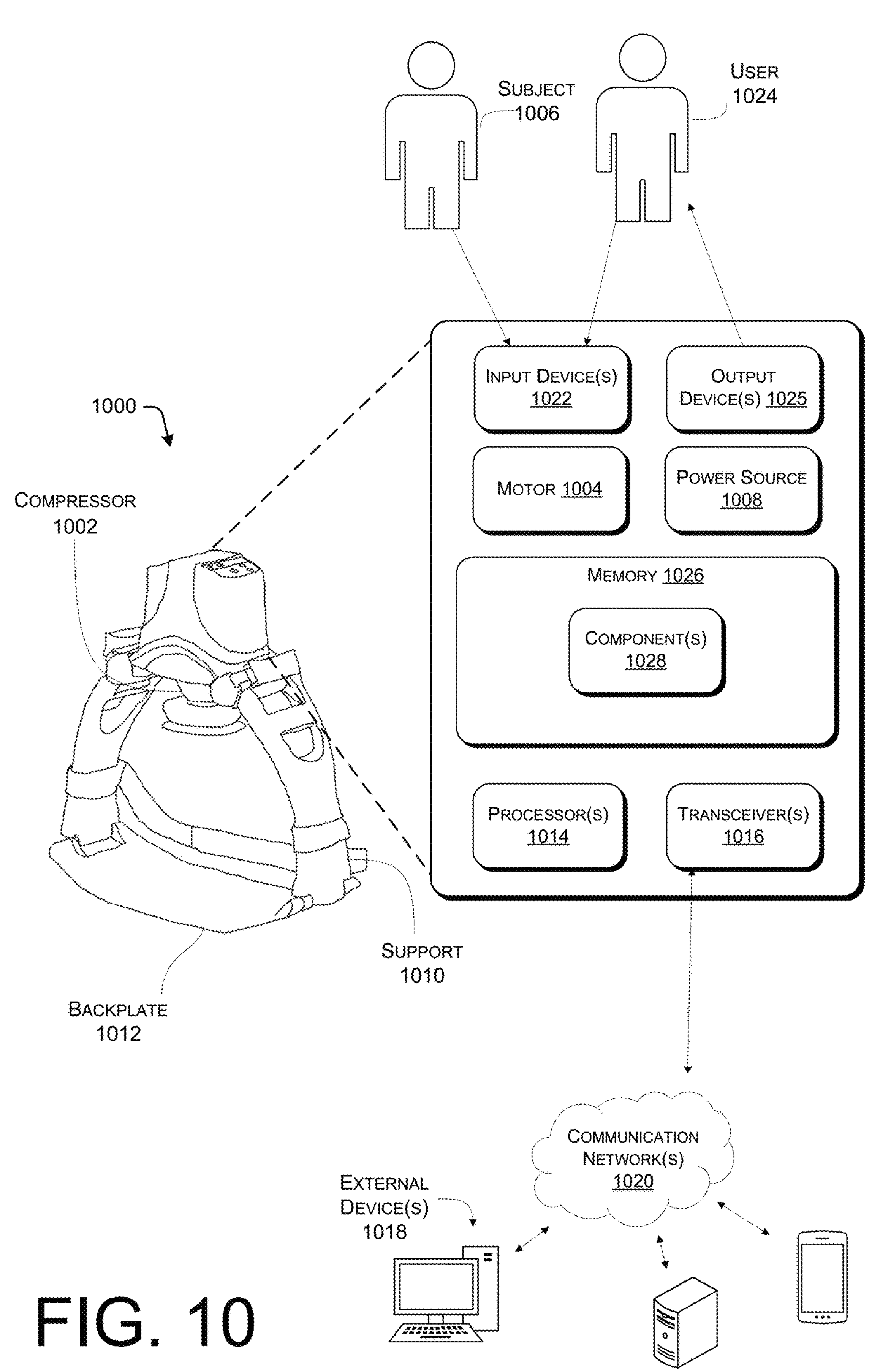
FIG. 10 illustrates a chest compression device configured to perform various functions described herein.

FIG. 10 illustrates a chest compression device 1000 configured to perform various functions described herein. For example, the chest compression device 1000 is the mechanical chest compression device 426 described with reference to FIG. 4.

In various implementations, the chest compression device 1000 includes a compressor 1002 that is operatively coupled to a motor 1004. The compressor 1002 physically administers a force to the chest of a subject 1006 that compresses the chest of the subject 1006. In some examples, the compressor 1002 includes at least one piston that periodically moves between two positions (e.g., a compressed position and a release position) at a compression frequency. For example, when the piston is positioned on the chest of the subject 1006, the piston compresses the chest when the piston is moved into the compressed position. A suction cup may be positioned on a tip of the piston, such that the suction cup contacts the chest of the subject 1006 during operation. In various cases, the compressor 1002 includes a band that periodically tightens to a first tension and loosens to a second tension at a compression frequency. For instance, when the band is disposed around the chest of the subject 1006, the band compresses the chest when the band tightens.

The motor 1004 is configured to convert electrical energy stored in a power source 1008 into mechanical energy that moves and/or tightens the compressor 1002, thereby causing the compressor 1002 to administer the force to the chest of the subject 1006. In various implementations, the power source 1008 is portable. For instance, the power source 1008 includes at least one rechargeable (e.g., lithium-ion) battery. In some cases, the power source 1008 supplies electrical energy to one or more elements of the chest compression device 1000 described herein.

In various cases, the chest compression device 1000 includes a support 1010 that is physically coupled to the compressor 1002, such that the compressor 1002 maintains a position relative to the subject 1006 during operation. In some implementations, the support 1010 is physically coupled to a backplate 1012, cot, or other external structure with a fixed position relative to the subject 1006. According to some cases, the support 1010 is physically coupled to a portion of the subject 1006, such as wrists of the subject 1006.

The operation of the chest compression device 1000 may be controlled by at least one processor 1014. In various implementations, the motor 1004 is communicatively coupled to the processor(s) 1014. Specifically, the processor(s) 1014 is configured to output a control signal to the motor 1004 that causes the motor 1004 to actuate or otherwise adjust the compressor 1002. For instance, the motor 1004 causes the compressor 1002 to administer the compressions to the subject 1006 based on the control signal. In some cases, the control signal indicates one or more treatment parameters of the compressions. Examples of treatment parameters include a frequency, timing, depth, force, position, velocity, and acceleration of the compressor 1002 administering the compressions. According to various cases, the control signal causes the motor 1004 to cease compressions, such as after ROSC has been detected.

In various implementations, the chest compression device 1000 includes at least one transceiver 1016 configured to communicate with at least one external device 1018 over one or more communication networks 1020. Any wired and/or wireless communication network described herein can be included in the communication network(s) 1020 illustrated in FIG. 10. The external device(s) 1018, for example, includes at least one of a flow monitor, a monitor-defibrillator, an AED, an ECMO device, a ventilation device, a subject monitor, a mobile phone, a server, or a computing device. In some implementations, the transceiver(s) 1016 is configured to communicate with the external device(s) 1018 by transmitting and/or receiving signals wirelessly. For example, the transceiver(s) 1016 includes a NIC, a network adapter, a LAN adapter, or a physical, virtual, or logical address to connect to the various external devices and/or systems. In various examples, the transceiver(s) 1016 includes any sort of wireless transceivers capable of engaging in wireless communication (e.g., RF communication). For example, the communication network(s) 1020 includes one or more wireless networks that include a 3GPP network, such as an LTE RAN (e.g., over one or more LTE bands), an NR RAN (e.g., over one or more NR bands), or a combination thereof. In some cases, the transceiver(s) 1016 includes other wireless modems, such as a modem for engaging in WI-FI®, WIGIG®, WIMAX®, BLUETOOTH®, or infrared communication over the communication network(s) 1020. The signals, in various cases, encode data in the form of data packets, datagrams, or the like. In some cases, the signals are transmitted as compressions are being administered by the chest compression device 1000 (e.g., for real-time feedback by the external device(s) 1018), after compressions are administered by the chest compression device 1000 (e.g., for post-event review at the external device 1018), or a combination thereof.

In various cases, the processor(s) 1014 generates the control signal based on data encoded in the signals received from the external device(s) 1018. For instance, the signals include an instruction to initiate the compressions, and the processor(s) 1014 instructs the motor 1004 to begin actuating the compressor 1002 in accordance with the signals.

In some cases, the chest compression device 1000 includes at least one input device 1022. In various examples, the input device(s) 1022 is configured to receive an input signal from a user 1024, who may be a rescuer treating the subject 1006. Examples of the input device(s) 1022 include, for instance, a switch, a keypad, a cursor control, a touch-sensitive display, a voice input device (e.g., a microphone), a haptic feedback device (e.g., a gyroscope), or any combination thereof. In various implementations, the processor(s) 1014 generate the control signal based on the input signal. For instance, the processor(s) 1014 generate the control signal to adjust a frequency of the compressions based on the chest compression device 1000 detecting a selection by the user 1024 of a user interface element displayed on a touchscreen or detecting the user 1024 pressing a button integrated with an external housing of the chest compression device 1000.

According to some examples, the input device(s) 1022 include one or more sensors. The sensor(s), for example, is configured to detect a physiological parameter of the subject 1006. In some implementations, the sensor(s) is configured to detect a state parameter of the chest compression device 1000, such as a position of the compressor 1002 with respect to the subject 1006 or the backplate 1012, a force administered by the compressor 1002 on the subject 1006, a force administered onto the backplate 1012 by the body of the subject 1006 during a compression, or the like. According to some implementations, the signals transmitted by the transceiver(s) 1016 indicate the physiological parameter(s) and/or the state parameter(s).

The chest compression device 1000 further includes at least one output device 1025, in various implementations. Examples of the output device(s) 1025 include, for instance, least one of a display (e.g., a projector, an LED screen, etc.), a speaker, a haptic output device, a printer, a light source such as an LED, or any combination thereof. In some implementations, the output device(s) 1025 include a screen configured to display various parameters detected by and/or reported to the chest compression device 1000, a charge level of the power source 1008, a timer indicating a time since compressions were initiated or paused, and other relevant information.

The chest compression device 1000 further includes memory 1026. In various implementations, the memory 1026 is volatile (such as RAM), non-volatile (such as ROM, flash memory, etc.) or some combination of the two. The memory 1026 stores instructions that, when executed by the processor(s) 1014, causes the processor(s) 1014 to perform various operations. In various examples, the memory 1026 stores methods, threads, processes, applications, objects, modules, any other sort of executable instruction, or a combination thereof. In some cases, the memory 1026 stores files, databases, or a combination thereof. In some examples, the memory 1026 includes, but is not limited to, RAM, ROM, EEPROM, flash memory, or any other memory technology. In some examples, the memory 1026 includes one or more of CD-ROMs, DVDs, CAM, or other optical storage, magnetic cassettes, magnetic tape, magnetic disk storage or other magnetic storage devices, or any other medium which can be used to store the desired information. In various cases, the memory 1026 stores instructions, programs, threads, objects, data, or any combination thereof, that cause the processor(s) 1014 to perform various functions. In various cases, the memory 1026 stores one or more parameters that are detected by the chest compression device 1000 and/or reported to the chest compression device 1000.

In implementations of the present disclosure, the memory 1026 also stores one or more components 1028. The component(s) 1028 include programs, instructions, files, databases, models, or any other type of data that causes the device 1000 to perform any of the functions described herein.

Figure 11:
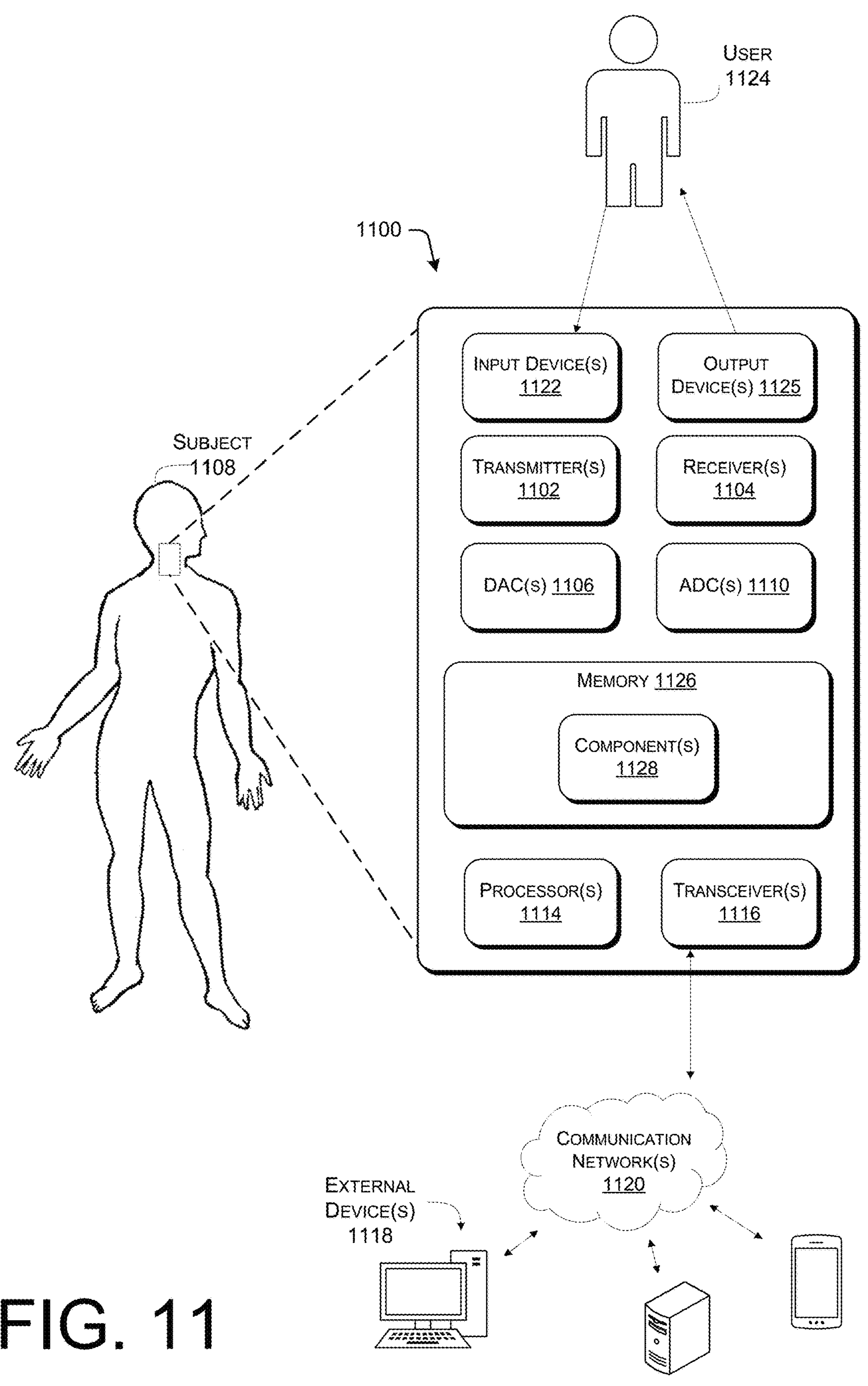
FIG. 11 illustrates a flow monitor configured to perform various functions described herein.

FIG. 11 illustrates a flow monitor 1100 configured to perform various functions described herein. For example, the flow monitor 1100 is the flow monitor 106 described with reference to FIG. 1 or the flow monitor 402 described above with reference to FIG. 4.

In various implementations, the flow monitor 1100 includes one or more transmitters 1102, one or more receivers 1104, one or more DACs 1106, and one or more digital to analog converters 1110. The transmitter(s) 1102 is configured to emit an incident beam into a subject 1108. The incident beam includes infrared light and/or ultrasound. For instance, the transmitter(s) 1102 include one or more light sources (e.g., one or more LEDs) or one or more piezoelectric crystals, MEMS transducers, or other electro-mechanical conversion device or material. In some examples, the flow monitor 1100 is positioned such that the incident beam is transmitted through a window in the skull of the subject 1108, such as a temple, an orbital cavity, a nasal cavity, or an ear canal. In some cases, the transmitter(s) 1102 emits one or more incident beams toward an artery supplying blood to a portion of the body of the subject 1108 and a vein transporting blood out of the portion of the body of the subject 1108.

In various implementations, the incident beam is reflected or otherwise scattered by blood in a blood vessel of the subject 1108. The receiver(s) 1104 is configured to detect within a return beam that includes signals from the reflection or scatter from the blood in the blood vessel. For example, the receiver(s) 1104 include one or more light sensors or one or more piezoelectric crystals, MEMS transducers, or other electro-mechanical conversion device or material. In various cases, the flow monitor 1100 includes one or more transceivers that embody the transmitter(s) 1102 and receiver(s) 1104.

The operation of the flow monitor 1100 may be controlled by at least one processor 1114. The processor(s) 1114 are communicatively coupled to the DAC(s) 1106 and the ADC(s) 1110. The DAC(s) 1106 is configured to convert digital signals output by the processor(s) 1114 into analog signals, such as analog signals that induce the transmitter(s) 1102 to emit the incident beam. The ADC(S) 1110 is configured to convert analog signals generated by the receiver(s) 1104 (e.g., induced by detecting the return beam) into digital signals that are received by the processor(s) 1114. The processor(s) 1114 is configured to control the transmitter(s) 1102 and to analyze the signals detected by the receiver(s) 1104. The processor(s) 1114, for instance, analyze the digital signals from the ADC(s) 1110, which are indicative of the return beam detected by the receiver(s)

1104, in order to determine a flow velocity of the blood through the blood vessel. In some examples, the flow monitor 1100 includes one or more switches (e.g., MOSFETs) connected to an array of transmitters within the transmitter(s) 1102 that respectively connect the transmitter(s) 1102 between one or more power rails (e.g., negative and/or positive power rails) and ground. The processor(s) 1114, for instance, cause the switch(es) to connect each transmitter among the transmitter(s) 1102 between ground and the power rail(s) in a periodic waveform, which causes the transmitter(s) 1102 to selectively output incident beam(s) in accordance with the periodic waveform. In some cases, the waveform has a three half-cycle waveform and goes from a positive voltage, to a negative voltage, to a positive voltage, then to ground. In some cases, more than one positive power rail or more than one negative power rail is used for the same waveform.

In various implementations, the flow monitor 1100 includes at least one transceiver 1116 configured to communicate with at least one external device 1118 over one or more communication networks 1120. Any communication network described herein can be included in the communication network(s) 1120 illustrated in FIG. 11. The external device(s) 1118, for example, includes at least one of a mechanical chest compression device, a monitor-defibrillator, an AED, an ECMO device, a ventilation device, a subject monitor, a mobile phone, a server, or a computing device. In some implementations, the transceiver(s) 1116 is configured to communicate with the external device(s) 1118 by transmitting and/or receiving signals in a wired fashion and/or wirelessly. For example, the transceiver(s) 1116 includes a NIC, a network adapter, a LAN adapter, or a physical, virtual, or logical address to connect to the various external devices and/or systems. In various examples, the transceiver(s) 1116 includes any sort of wireless transceivers capable of engaging in wireless communication (e.g., RF communication). For example, the communication network(s) 1120 includes one or more wireless networks that include a 3GPP network, such as an LTE RAN (e.g., over one or more LTE bands), an NR RAN (e.g., over one or more NR bands), or a combination thereof. In some cases, the transceiver(s) 1116 includes other wireless modems, such as a modem for engaging in WI-FI®, WIGIG®, WIMAX®, BLUETOOTH®, or infrared communication over the communication network(s) 1120. The signals, in various cases, encode data in the form of data packets, datagrams, or the like. In some cases, the signals are transmitted as compressions are being administered by the flow monitor 1100 (e.g., for real-time feedback by the external device(s) 1118), after compressions are administered by the flow monitor 1100 (e.g., for post-event review at the external device 1118), or a combination thereof.

In various cases, the processor(s) 1114 generates the control signal based on data encoded in the signals received from the external device(s) 1118. For instance, the signals include an instruction to initiate monitoring, and the processor(s) 1114 outputs a control signal that causes the transmitter(s) 1102 to emit the incident beam.

In some cases, the flow monitor 1100 includes at least one input device 1122. In various examples, the input device(s) 1122 is configured to receive an input signal from a user 1124, who may be a rescuer treating the subject 1108. Examples of the input device(s) 1122 include, for instance, a a keypad, a cursor control, a touch-sensitive display, a voice input device (e.g., a microphone), a haptic feedback device (e.g., a gyroscope), or any combination thereof. In various implementations, the processor(s) 1114 generate the control signal based on the input signal. For instance, the processor(s) 1114 generate the control signal to adjust a frequency of the compressions based on the flow monitor 1100 detecting a selection by the user 1124 of a user interface element displayed on a touchscreen or detecting the user 1124 pressing a button integrated with an external housing of the flow monitor 1100.

According to some examples, the input device(s) 1122 include one or more sensors. The sensor(s), for example, is configured to detect a physiological parameter of the subject 1108. In some cases, the sensor(s) include one or more microphones, one or more accelerometers, one or more oximetry sensors, or one or more ECG sensors. The sensor (s), for instance, is configured to detect one or more physiological parameters. In some implementations, the sensor(s) is configured to detect a state parameter of the flow monitor 1100, such as a position of the flow monitor 1100 with respect to the subject 1108 or the like. According to some implementations, the signals transmitted by the transceiver(s) 1116 indicate the physiological parameter(s) and/or the state parameter(s).

The flow monitor 1100 further includes at least one output device 1125, in various implementations. Examples of the output device(s) 1125 include, for instance, least one of a display (e.g., a projector, an LED screen, etc.), a speaker, a haptic output device, a printer, a light such as an LED, or any combination thereof. In some implementations, the output device(s) 1125 include a screen configured to display various parameters detected by and/or reported to the flow monitor 1100, a battery level of the flow monitor 1100, and other relevant information.

The flow monitor 1100 further includes memory 1126. In various implementations, the memory 1126 is volatile (such as RAM), non-volatile (such as ROM, flash memory, etc.) or some combination of the two. The memory 1126 stores instructions that, when executed by the processor(s) 1114, causes the processor(s) 1114 to perform various operations. In various examples, the memory 1126 stores methods, threads, processes, applications, objects, modules, any other sort of executable instruction, or a combination thereof. In some cases, the memory 1126 stores files, databases, or a combination thereof. In some examples, the memory 1126 includes, but is not limited to, RAM, ROM, EEPROM, flash memory, or any other memory technology. In some examples, the memory 1126 includes one or more of CD-ROMs, DVDs, CAM, or other optical storage, magnetic cassettes, magnetic tape, magnetic disk storage or other magnetic storage devices, or any other medium which can be used to store the desired information. In various cases, the memory 1126 stores instructions, programs, threads, objects, data, or any combination thereof, that cause the processor(s) 1114 to perform various functions. In various cases, the memory 1126 stores one or more parameters that are detected by the flow monitor 1100 and/or reported to the flow monitor 1100.

In implementations of the present disclosure, the memory 1126 also stores one or more components 1128. The component(s) 1128 include programs, instructions, files, databases, models, or any other type of data that causes the flow monitor 1100 to perform any of the functions described herein.

EXAMPLE CLAUSES

1. A blood flow monitoring system, including: a first transmitter configured to emit a first incident beam; a first receiver configured to detect a reflection of the first incident beam from an artery of a subject during a time interval; a second transmitter configured to emit a second incident beam; a second receiver configured to detect a reflection of the second incident beam from a vein of the subject during the time interval; a display; and a processor configured to: detect, by analyzing the reflection of the first incident beam, blood flow through the artery during the time interval; detect, by analyzing the reflection of the second incident beam, blood flow through the vein during the time interval; determine a ratio of an amplitude of the blood flow through the artery during the time interval and an amplitude of the blood flow through the vein during the time interval; determine that the subject received a chest compression during the time interval by determining that the ratio is greater than a threshold; and cause the display to visually output an indication of the chest compression.

2. The blood flow monitoring system of clause 1, further including: a housing; and an adhesive configured to attach the housing to a neck of the subject, wherein the artery includes a carotid artery and the vein includes a jugular vein.

3. The blood flow monitoring system of clause 1 or 2, the time interval being a first time interval, wherein the first receiver is configured to detect a reflection of the first incident beam from the artery of the subject during a second time interval, wherein the second receiver is configured to detect a reflection of the second incident beam from the vein of the subject during the second time interval, and wherein the processor is further configured to: determine, by analyzing the reflection of the first incident beam from the artery of the subject during the second time interval, a direction of blood flowing through the artery during the second time interval; determine, by analyzing the reflection of the second incident beam from the vein of the subject during the second time interval, a direction of blood flowing through the vein during the second time interval; determine that blood is spontaneously circulating in the subject by comparing the direction of blood flowing through the artery during the second time interval and the direction of blood flowing through the vein during the second time interval; and cause the display to visually output an indication that blood is spontaneously circulating in the subject.

4. A method, including: detecting blood flow through an artery of a subject during a time interval; detecting blood flow through a vein of the subject during the time interval; and determining whether blood is spontaneously flowing through a body of the subject by comparing the blood flow through the artery of the subject during the time interval and the blood flow through the vein of the subject during the time interval.

5. The method of clause 4, wherein detecting the blood flow through the artery of the subject during the time interval includes determining a Doppler shift of a first ultrasound beam reflected from blood in the artery, and wherein detecting the blood flow through the vein of the subject during the time interval includes determining a Doppler shift of the first ultrasound beam or a second ultrasound beam reflected from blood in the vein.

6. The method of clause 4 or 5, wherein the artery and the vein are substantially parallel to each other.

7. The method of any of clauses 4 to 6, wherein the artery includes a carotid artery and the vein includes a jugular vein.

8. The method of any of clauses 4 to 7, wherein determining whether blood is spontaneously flowing through the body of the subject by comparing the blood flow through the artery of the subject during the time interval and a direction of blood flow through the vein of the subject during the time interval includes: determining that both a direction of the blood flow through the artery of the subject during the time interval and a direction of the blood flow through the vein of the subject are away from a heart of the subject or toward the heart of the subject; and in response to determining that both the direction of the blood flow through the artery of the subject during the time interval and the direction of the blood flow through the vein of the subject are away from a heart of the subject or toward the heart of the subject, determining that the subject has received a chest compression during the time interval.

9. The method of any of clauses 4 to 8, wherein determining whether blood is spontaneously flowing through the body of the subject by comparing the blood flow through the artery of the subject during the time interval and the blood flow through the vein of the subject during the time interval includes: determining that the blood flow through the vein during the time interval is indicative of pulsatile flow; and in response to determining that the blood through the vein during the time interval is indicative of pulsatile flow, determining that the subject has received a chest compression during the time interval.

10. The method of any of clauses 4 to 9, wherein determining whether blood is spontaneously flowing through the body of the subject by comparing the blood flow through the artery of the subject during the time interval and the blood flow through the vein of the subject during the time interval includes: determining an amplitude of the blood flow through the artery during the time interval; determining an amplitude of the blood flow through the vein during the time interval; determining a ratio of the amplitude of the blood flow through the artery during the time interval and the amplitude of the blood flow through the vein during the time interval; determining that the ratio is below a threshold; and in response to determining that the ratio is below the threshold, determining that the subject has a received a chest compression during the time interval.

11. The method of any of clauses 4 to 10, wherein determining whether blood is spontaneously flowing through the body of the subject by comparing the blood flow through the artery of the subject during the time interval and the blood flow through the vein of the subject during the time interval includes: determining that a direction of the blood flow through the artery of the subject during the time interval is different than a direction of the blood flow through the vein of the subject; and in response to determining that the direction of the blood flow through the artery of the subject during the time interval is different than the direction of the blood flow through the vein of the subject, determining that blood is spontaneously flowing through the body of the subject.

12. The method of any of clauses 4 to 11, wherein determining whether blood is spontaneously flowing through the body of the subject by comparing the blood flow through the artery of the subject during the time interval and the blood flow through the vein of the subject during the time interval includes: determining that the blood flow through the vein during the time interval is non-pulsatile; and in response to determining that the blood through the vein during the time interval is non-pulsatile, determining that blood is spontaneously flowing through the body of the subject.

13. The method of any of clauses 4 to 12, wherein determining whether blood is spontaneously flowing through the body of the subject by comparing the blood flow through the artery of the subject during the time interval and the blood flow through the vein of the subject during the time interval includes: determining an amplitude of the blood flow through the artery during the time interval; determining an amplitude of the blood flow through the vein during the time interval; determining a ratio of the amplitude of the blood flow through the artery during the time interval and the amplitude of the blood flow through the vein during the time interval; determining that the ratio is above a threshold; and in response to determining that the ratio is above the threshold, determining that blood is spontaneously flowing through the body of the subject.

14. The method of any of clauses 4 to 13, further including: determining a velocity or volume of the blood flow through the artery during the time interval; determining a velocity or volume of the blood flow through the vein during the time interval; determining an efficacy of chest compression administered during the time interval by analyzing the velocity or volume of the blood flow through the artery during the time interval and the velocity or volume of the blood flow through the vein during the time interval; and outputting an indication of the efficacy of the chest compression.

15. The method of any of clauses 4 to 14, wherein determining whether blood is spontaneously flowing through the body of the subject by comparing the blood flow through the artery of the subject during the time interval and the blood flow through the vein of the subject during the time interval includes: determining that a direction of the blood flow through the artery of the subject during the time interval is away from a heart of the subject; determining that a direction of the blood flow through the vein of the subject during the time interval is toward the heart of the subject; and in response to determining that the direction of the blood flow through the artery of the subject during the time interval is away from the heart of the subject and determining that the direction of the blood flow through the vein of the subject during the time interval is toward the heart of the subject, determining that blood is spontaneously flowing through the body of the subject.

16. The method of clause 15, further including: in response to determining that blood is spontaneously flowing through the body of the subject, outputting an instruction to cease chest compressions on the subject.

17. The method of any of clauses 4 to 16, further including: outputting, to a user, an indication of whether blood is spontaneously flowing through the body of the subject.

18. A device, including: a first sensor configured to detect blood flow through an artery of a subject during a time interval; a second sensor configured to detect blood flow through a vein of the subject during the time interval; and a processor configured to determine whether blood is spontaneously flowing through a body of the subject by comparing the blood flow through the artery of the subject during the time interval and the blood flow through the vein of the subject during the time interval.

19. The device of clause 18, wherein the first sensor is configured to detect the blood flow through the artery by detecting a Doppler shift of a first beam reflected from blood in the artery, and wherein the second sensor is configured to detect the blood flow through the vein by detecting a Doppler shift of a second beam reflected from blood in the vein.

20. The device of clause 19, wherein the first beam includes a first ultrasound beam or a first infrared beam, and wherein the second beam includes a second ultrasound beam or a second infrared beam.

21. The device of any of clauses 18 to 20, wherein the processor is configured to determine whether blood is spontaneously flowing through a body of the subject by determining that a direction of the blood flow through the artery of the subject during the time interval is parallel to a direction of blood flow through the vein of the subject during the time interval.

22. The device of any of clauses 18 to 21, wherein the processor is configured to determine whether blood is spontaneously flowing through a body of the subject by: determining that the blood flow through the vein during the time interval is indicative of pulsatile flow; and in response to determining that the blood through the vein during the time interval is indicative of pulsatile flow, determining that the subject has received a chest compression during the time interval.

23. The device of any of clauses 18 to 22, wherein the processor is configured to determine whether blood is spontaneously flowing through a body of the subject by: determining an amplitude of the blood flow through the artery during the time interval; determining an amplitude of the blood flow through the vein during the time interval; determining a ratio of the amplitude of the blood flow through the artery during the time interval and the amplitude of the blood flow through the vein during the time interval; determining that the ratio is below a threshold; and in response to determining that the ratio is below the threshold, determining that the subject has a received a chest compression during the time interval.

24. The device of clause 23, wherein the processor is further configured to: determine a velocity or volume of the blood flow through the artery during the time interval; determine a velocity or volume of the blood flow through the vein during the time interval; determine an efficacy of a chest compression by analyzing the velocity or volume of the blood flow through the artery during the time interval and the velocity or volume of the blood flow through the vein during the time interval; and output an indication of the efficacy of the chest compression.

25. The device of any of clauses 18 to 24, wherein the processor is configured to determine that blood is spontaneously flowing through the body of the subject by: determining that a direction of the blood flow through the artery of the subject during the time interval is away from a heart of the subject; and determining that a direction of the blood flow through the vein of the subject during the time interval is toward the heart of the subject.

26. The device of any of clauses 18 to 25, further including: an output device configured to output, to a user, an indication of whether the blood is flowing through the body of the subject; and in response to determining that blood is spontaneously flowing through the body of the subject, outputting an instruction to cease chest compressions on the subject.

27. The device of any of clauses 18 to 26, further including: a housing; and an adhesive disposed on the housing, the adhesive being configured to adhere the device to skin of the subject.

28. A resuscitation system, including: a mechanical chest compression device configured to administer chest compressions to a subject during a time interval; and a flow monitor including: a housing; an adhesive disposed on the housing and configured to attach the flow monitor to a neck of the subject; a transmitter configured to output an ultrasound beam toward a carotid artery of the subject; a receiver configured to generate an analog signal by detecting a reflection of the ultrasound beam from blood flowing through the carotid artery of the subject during the time interval; a processor configured to: determine a velocity of the blood flowing through the carotid artery by analyzing the analog signal; determine a volume of the blood flowing through the carotid artery by integrating the velocity flowing through the carotid artery over the time interval; determine that the volume of the blood flowing through the carotid artery is below a threshold; and in response to determining that the volume of the blood flowing through the carotid artery is below the threshold, cause the mechanical chest compression device to change a position of the chest compressions.

29. The resuscitation system of clause 28, wherein the blood flowing through the carotid artery is moving in a direction toward a brain of the subject.

30. The resuscitation system of clause 28 or 29, wherein the flow monitor further includes a transceiver, and wherein the processor is configured to cause the mechanical chest compression device to change a position of the chest compressions by causing the transceiver to wirelessly transmit, to the mechanical chest compression device, a communication signal instructing the mechanical chest compression device to change the position of the chest compressions.

31. A method, including: identifying a physiological parameter indicative of blood flow through a blood vessel of a subject during a time interval, the subject receiving chest compressions during the time interval; determining that the physiological parameter is below a lower threshold or above an upper threshold; and in response to determining that the physiological parameter is below the lower threshold or above the upper threshold, outputting an instruction to change a position of the chest compressions on the subject.

32. The method of clause 31, wherein the physiological parameter includes a velocity of the blood flow or a volume of the blood flow.

33. The method of clause 31 or 32, wherein identifying the physiological parameter indicative of blood flow through the blood vessel includes: detecting a Doppler shift of an incident beam and a reflection of the incident beam from blood in the blood vessel.

34. The method of any of clauses 31 to 33, wherein the blood vessel includes an artery.

35. The method of any of clauses 31 to 34, wherein outputting the instruction to change the position of the chest compressions on the subject includes outputting the instruction to a mechanical chest compression device.

36. The method of any of clauses 31 to 35, wherein outputting the instruction to change the position of the chest compressions on the subject includes outputting the instruction to a user.

37. The method of any of clauses 31 to 36, wherein outputting the instruction to change the position of the chest compressions on the subject further includes outputting an instruction to change the a frequency of the chest compressions administered to the subject.

38. The method of any of clauses 31 to 37, wherein outputting the instruction to change the position of the chest compressions on the subject further includes outputting an instruction to change a depth of the chest compressions administered to the subject.

39. The method of any of clauses 31 to 38, wherein outputting the instruction to change the position of the chest compressions on the subject further includes outputting an instruction to change a duty cycle, speed, or height of recoil of the chest compressions.

40. A device, including: a sensor configured to detect a physiological parameter indicative of blood flow through a blood vessel of a subject during a time interval, the subject receiving chest compressions during the time interval; and a processor configured to: determine that the physiological parameter is below a lower threshold or above an upper threshold; and in response to determining that the parameter is below the lower threshold or above the upper threshold, output an instruction to change a position of the chest compressions on the subject.

41. The device of clause 40, wherein the physiological parameter includes a velocity of the blood flow or a volume of the blood flow.

42. The device of clause 40 or 41, wherein identifying the physiological parameter indicative of blood flow through the blood vessel includes: detecting a Doppler shift of an incident beam and a reflection of the incident beam from blood in the blood vessel.

43. The device of any of clauses 40 to 42, wherein the blood vessel includes an artery.

44 The device of any of clauses 40 to 43, wherein the instruction to change the position of the chest compressions on the subject further includes an instruction to change a frequency of the chest compressions administered to the subject, a depth of the chest compressions administered to the subject, a duty cycle of the chest compressions administered to the subject, a speed of the chest compressions administered to the subject, or a height of recoil of the chest compressions administered to the subject.

45. The device of any of clauses 40 to 44, further including: a transceiver, wherein the processor is configured to output the instruction to change the position of the chest compressions on the subject by causing the transceiver to transmit, to an external device, a signal indicating the instruction.

46. The device of clause 45, wherein the external device includes a mechanical chest compression device.

47. The device of any of clauses 40 to 46, further including: an output device, wherein the processor is configured to output the instruction to change the chest compression parameter includes causing the output device to output the instruction to a user.

48. A flow monitor, including: a housing; an adhesive disposed on the housing and configured to attach the flow monitor to a neck of the subject; a first flow monitor configured to detect a velocity of blood flowing through a carotid artery of the subject; a second flow monitor configured to detect a velocity of blood flowing through a jugular vein of the subject; a compressions sensor configured to detect a first chest compression and a second chest compression administered to the subject; a display; and a processor configured to: determine a volume of blood flowing to a brain of the subject by analyzing the velocity of blood flowing through a carotid artery of the subject; determine a volume of blood flowing from the brain of the subject by analyzing the velocity of blood flowing through the jugular vein of the subject; determine a net volume of blood to the brain by determining a difference of the volume of blood to the brain of the subject and the volume of blood from the brain of the subject; cause the display to visually present a first waveform indicating the net volume of blood to the brain during the first chest compression; and cause the display to visually present a second waveform indicating the net volume of blood to the brain during the second chest compression, the second waveform being aligned with the first waveform.

49. The flow monitor of clause 48, further including: a transceiver configured to transmit a signal indicating the first waveform and the second waveform.

50. The flow monitor of clause 48 or 49, further including: an input device configured to detect an input signal indicating a treatment performed on the subject, wherein the processor is further configured to cause the display to visually present an indication of the net volume of blood to the brain at a time of the treatment.

51. A method, including: identifying first data including measurements of blood flowing through a first blood vessel of a subject; identifying second data including measurements of blood flowing through a second blood vessel of the subject; and displaying an image indicating the first data and the second data.

52. The method of clause 51, wherein the measurements of blood flowing through a first blood vessel of a subject include flow velocity measurements or net volume measurements, and wherein the measurements of blood flowing through the first blood vessel of the subject include flow velocity measurements or net volume measurements.

53. The method of clause 51 or 52, further including: detecting a chest compression performed on the subject.

54. The method of clause 53, wherein the image includes a cross-sectional image of the first blood vessel and the second blood vessel, the cross-sectional image including: a first portion corresponding to heart-induced blood flow; or a second portion corresponding to chest-compression induced blood flow, the second portion having a different color than the first portion.

55. The method of clause 53 or 54, wherein the image includes: a waveform indicating the first data or the second data; and a shape overlying the waveform, the shape indicating the chest compression.

56. The method of any of clauses 51 to 55, further including: detecting a first chest compression performed on the subject or a first QRS complex of the subject; and detecting a second chest compression performed on the subject or a second QRS complex of the subject, wherein displaying the image indicating the first data and the second data includes: displaying a first waveform indicating a portion of the first data detected during the first chest compression or the first QRS complex; and displaying a second waveform indicating a portion of the second data detected during the second chest compression or the second QRS complex.

57. The method of any of clauses 51 to 56, further including: determining a condition of the subject by comparing the first data and/or the second data to a threshold, wherein the image includes a text or numeric indicator of the condition.

58. The method of any of clauses 51 to 57, further including: outputting a first audio channel indicating the first data; and outputting a second audio channel indicating the second data.

59. The method of any of clauses 51 to 58, further including: transmitting, to an external device, a signal indicating the image.

60. A medical device configured to perform the method of any of clauses 51 to 59.

61. A method, including: detecting a volume of blood displaced through a cross-section of a blood vessel during a time period; and determining that the blood is spontaneously circulating by comparing the volume of blood displaced through the cross-section of the blood vessel during the time period to a threshold.

62. The method of clause 61, wherein the blood vessel is disposed in a body of a subject that is receiving chest compressions during the time period.

63. The method of clause 61 or 62, wherein the blood vessel is an artery, the volume of blood is a net volume of blood displaced through the cross-section of the artery in a direction away from a heart.

64. The method of clause 63, wherein determining that the blood is spontaneously circulating by determining that the volume of blood displaced through the cross-section of the artery during the time period is above a threshold.

65. The method of any of clauses 61 to 64, wherein the blood vessel is a vein, the volume of blood is a net volume of blood displaced through the cross-section of the vein in a direction toward a heart.

66. The method of clause 65, wherein determining that the blood is spontaneously circulating by determining that the volume of blood displaced through the cross-section of the vein during the time period is above the threshold.

67. The method of any of clauses 61 to 66, further including: in response to determining that the blood is spontaneously circulating, outputting an instruction to cease administering chest compressions.

68. The method of any of clauses 61 to 67, further including: in response to determining that the blood is spontaneously circulating, pause administration of chest compressions.

69. The method of any of clauses 61 to 68, further including: outputting an indication that the blood is spontaneously circulating.

70. A medical device configured to perform the method of any of clauses 61 to 69.

71. A method, including: detecting a blood flow through a cross-section of a blood vessel with respect to time; determining a peak or mean of the blood flow through the cross-section of the blood flow with respect to time; and determining that the blood flow is spontaneously circulating by analyzing: whether the blood flow is pulsatile; and whether the peak or the mean of the blood flow exceeds a threshold.

72. The method of clause 71, wherein the blood vessel is an artery, the blood flow is directed away from a heart, the blood flow is pulsatile, and the peak of the blood flow exceeds the threshold.

73. The method of clause 72, wherein the artery is disposed in a subject receiving chest compressions.

74. The method of any of clauses 71 to 73, wherein the blood vessel is a vein, the blood flow is directed toward a heart, the blood flow is non-pulsatile, and the mean of the blood flow exceeds the threshold.

75. The method of any of clauses 71 to 74, wherein the blood vessel is disposed in a subject that is not receiving chest compressions.

76. The method of any of clauses 71 to 75, further including: in response to determining that the blood is spontaneously circulating, outputting an instruction to cease administering chest compressions.

77. The method of any of clauses 71 to 76, further including: in response to determining that the blood is spontaneously circulating, pause administration of chest compressions.

78. The method of any of clauses 71 to 77, further including: outputting an indication that the blood is spontaneously circulating.

79. A medical device configured to perform the method of any of clauses 71 to 78.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventors expect skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

What is claimed is:

1. A method, comprising:

detecting an amplitude of blood flow through an artery of a subject during a time interval;

detecting an amplitude of blood flow through a vein of the subject during the time interval;

determining a ratio of the amplitude of the blood flow through the artery during the time interval and the amplitude of the blood flow through the vein during the time interval; and determining whether blood is spontaneously flowing through a body of the subject by comparing the ratio to a threshold.

2. The method of claim 1, wherein detecting the amplitude of the blood flow through the artery of the subject during the time interval comprises determining a Doppler shift of a first ultrasound beam reflected from blood in the artery, and wherein detecting the amplitude of the blood flow through the vein of the subject during the time interval comprises determining a Doppler shift of the first ultrasound beam or a second ultrasound beam reflected from blood in the vein.

3. The method of claim 1, wherein the artery and the vein are parallel to each other.

4. The method off claim 1, wherein the artery comprises a carotid artery and the vein comprises a jugular vein.

5. The method of claim 1, wherein determining whether blood is spontaneously flowing through the body of the subject further comprises:

determining that both a direction of the blood flow through the artery of the subject during the time interval and a direction of the blood flow through the vein of the subject are away from a heart of the subject or toward the heart of the subject; and in response to determining that both the direction of the blood flow through the artery of the subject during the time interval and the direction of the blood flow through the vein of the subject are away from a heart of the subject or toward the heart of the subject, determining that the subject has received a chest compression during the time interval.

6. The method of claim 1, wherein determining whether blood is spontaneously flowing through the body of the subject further comprises:

determining that the blood flow through the vein during the time interval is indicative of pulsatile flow; and in response to determining that the blood through the vein during the time interval is indicative of pulsatile flow, determining that the subject has received a chest compression during the time interval.

7. The method of claim 1, wherein determining whether blood is spontaneously flowing through the body of the subject by comparing the ratio to the threshold comprises:

determining that the ratio is below the threshold; and in response to determining that the ratio is below the threshold, determining that the subject has a received a chest compression during the time interval.

8. The method of claim 1, wherein determining whether blood is spontaneously flowing through the body of the subject further comprises:

determining that a direction of the blood flow through the artery of the subject during the time interval is different than a direction of the blood flow through the vein of the subject; and in response to determining that the direction of the blood flow through the artery of the subject during the time interval is different than the direction of the blood flow through the vein of the subject, determining that blood is spontaneously flowing through the body of the subject.

9. The method of claim 1, wherein determining whether blood is spontaneously flowing through the body of the subject further comprises:

determining that the blood flow through the vein during the time interval is non-pulsatile; and in response to determining that the blood through the vein during the time interval is non-pulsatile, determining that blood is spontaneously flowing through the body of the subject.

10. The method of claim 1, wherein determining whether blood is spontaneously flowing through the body of the subject by comparing the ratio to the threshold comprises:

determining that the ratio is above the threshold; and in response to determining that the ratio is above the threshold, determining that blood is spontaneously flowing through the body of the subject.

11. The method of claim 1, further comprising:

determining a velocity or volume of the blood flow through the artery during the time interval;

determining a velocity or volume of the blood flow through the vein during the time interval;

determining an efficacy of chest compression administered during the time interval by analyzing the velocity or volume of the blood flow through the artery during the time interval and the velocity or volume of the blood flow through the vein during the time interval; and outputting an indication of the efficacy of the chest compression.

12. The method of claim 1, wherein determining whether blood is spontaneously flowing through the body of the subject further comprises:

determining that a direction of the blood flow through the artery of the subject during the time interval is away from a heart of the subject;

determining that a direction of the blood flow through the vein of the subject during the time interval is toward the heart of the subject; and in response to determining that the direction of the blood flow through the artery of the subject during the time interval is away from the heart of the subject and determining that the direction of the blood flow through the vein of the subject during the time interval is toward the heart of the subject, determining that blood is spontaneously flowing through the body of the subject.

13. The method of claim 12, further comprising:

in response to determining that blood is spontaneously flowing through the body of the subject, outputting an instruction to cease chest compressions on the subject.

14. A device comprising:

a first sensor configured to detect an amplitude of blood flow through an artery of a subject during a time interval;

a second sensor configured to detect an amplitude of blood flow through a vein of the subject during the time interval; and a processor configured to:

determine a ratio of the amplitude of the blood flow through the artery during the time interval and the amplitude of the blood flow through the vein during the time interval; and determine whether blood is spontaneously flowing through a body of the subject by comparing the ratio to a threshold.

15. The device of claim 14, wherein the processor is configured to determine whether the blood is spontaneously flowing through the body of the subject by determining that a direction of the blood flow through the artery of the subject during the time interval is parallel to a direction of blood flow through the vein of the subject during the time interval.

16. The device of claim 14, wherein the processor is configured to determine whether the blood is spontaneously flowing through the body of the subject by:

determining that the blood flow through the vein during the time interval is indicative of pulsatile flow; and in response to determining that the blood through the vein during the time interval is indicative of pulsatile flow, determining that the subject has received a chest compression during the time interval.

17. The device of claim 14, wherein the processor is configured to determine whether the blood is spontaneously flowing through the body of the subject by:

determining that the ratio is below the threshold; and in response to determining that the ratio is below the threshold, determining that the subject has a received a chest compression during the time interval.

18. The device of claim 17, further comprising:

a display, wherein the first sensor comprises:

a first transmitter configured to emit a first incident beam;

a first receiver configured to detect a reflection of the first incident beam from the artery of the subject during the time interval, the amplitude of the blood flow through the artery being dependent on the reflection of the first incident beam, wherein the second sensor comprises:

a second transmitter configured to emit a second incident beam;

a second receiver configured to detect a reflection of the second incident beam from the vein of the subject during the time interval, the amplitude of the blood flow through the vein being dependent on the reflection of the second incident beam, and wherein the processor is further configured to cause the display to visually output an indication of the chest compression.

19. The device of claim 18, further comprising:

a housing; and an adhesive configured to attach the housing to a neck of the subject, wherein the artery comprises a carotid artery and the vein comprises a jugular vein.

20. The device of claim 18, the time interval being a first time interval, wherein the first receiver is configured to detect a reflection of the first incident beam from the artery of the subject during a second time interval, wherein the second receiver is configured to detect a reflection of the second incident beam from the vein of the subject during the second time interval, and wherein the processor is further configured to:

determine, by analyzing the reflection of the first incident beam from the artery of the subject during the second time interval, a direction of blood flowing through the artery during the second time interval;

determine, by analyzing the reflection of the second incident beam from the vein of the subject during the second time interval, a direction of blood flowing through the vein during the second time interval;

determine that blood is spontaneously circulating in the subject by comparing the direction of blood flowing through the artery during the second time interval and the direction of blood flowing through the vein during the second time interval; and cause the display to visually output an indication that blood is spontaneously circulating in the subject.

* * * * *